(12) United States Patent  
Yukawa et al.

(10) Patent No.: US 8,722,311 B2
(45) Date of Patent: May 13, 2014

(54) POSITIVE RESIST COMPOSITION AND METHOD FOR PRODUCING MICROLENS

(75) Inventors: Shojiro Yukawa, Funabashi (JP); Shinya Arase, Funabashi (JP); Toshiaki Takeyama, Funabashi (JP); Yuki Endo, Funabashi (JP); Takeo Moro, Tokyo (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/574,938

(22) PCT Filed: Jan. 19, 2011

(86) PCT No.: PCT/JP2011/050854
§ 371 (c)(1),
(2), (4) Date: Jul. 24, 2012

(87) PCT Pub. No.: WO2011/093188
PCT Pub. Date: Aug. 4, 2011

(65) Prior Publication Data
US 2012/0292487 A1    Nov. 22, 2012

(30) Foreign Application Priority Data

Jan. 26, 2010   (JP) ................................ 2010-014505

(51) Int. Cl.
| | | |
|---|---|---|
| G03F 7/022 | (2006.01) | |
| G03F 7/027 | (2006.01) | |
| G03F 7/039 | (2006.01) | |
| G03F 7/30 | (2006.01) | |
| G03F 7/38 | (2006.01) | |

(52) U.S. Cl.
USPC ........ 430/280.1; 430/189; 430/192; 430/193; 430/288.1; 430/321; 430/326; 430/330; 430/905; 430/919; 430/927

(58) Field of Classification Search
None
See application file for complete search history.

(56) References Cited

U.S. PATENT DOCUMENTS

| | | | |
|---|---|---|---|
| 5,101,264 A | | 3/1992 | Kauchi et al. |
| 2004/0043322 A1 | | 3/2004 | Takahashi et al. |
| 2007/0295956 A1 | | 12/2007 | Haitko |
| 2007/0295983 A1 | | 12/2007 | Haitko |
| 2007/0299162 A1 | | 12/2007 | Haitko |
| 2008/0038662 A1* | | 2/2008 | Hatakeyama et al. ..... 430/270.1 |
| 2008/0097032 A1* | | 4/2008 | Ito et al. ....................... 525/185 |

FOREIGN PATENT DOCUMENTS

| | | |
|---|---|---|
| JP | A-1-251745 | 10/1989 |
| JP | A-4-166944 | 6/1992 |
| JP | A-6-095386 | 4/1994 |
| JP | A-2008-007782 | 1/2008 |
| WO | WO 03/029898 A1 | 4/2003 |

OTHER PUBLICATIONS

Feb. 22, 2011 English-language translation of Written Opinion issued in International Patent Application No. PCT/JP2011/050854.
Feb. 22, 2011 International Search Report issued in International Patent Application PCT/JP2011/050854.

* cited by examiner

*Primary Examiner* — Sin J. Lee
(74) *Attorney, Agent, or Firm* — Oliff PLC

(57) ABSTRACT

There is provided a resist composition suitable for forming a microlens which is excellent in transparency, heat resistance, and sensitivity characteristics, excellent in solubility in a developer, and as the result thereof has high resolution. A positive resist composition comprising; a component (A): an alkali-soluble polymer; a component (B): a compound having an organic group to be photolyzed to generate an alkali-soluble group; a component (C): a crosslinkable compound of Formula (1):

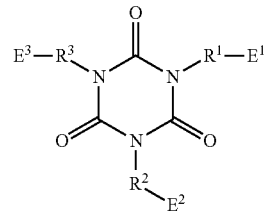

Formula (1)

[where $R^1$, $R^2$, and, $R^3$ are independently a $C_{1-6}$ alkylene group or oxyalkylene group which are optionally branched; and $E^1$, $E^2$, and $E^3$ are independently a group containing a structure of Formula (2) or Formula (3):

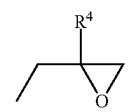

Formula (2)

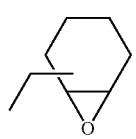

Formula (3)

(where $R^4$ is a hydrogen atom or a methyl group)]; and a component (D): a solvent.

10 Claims, No Drawings

POSITIVE RESIST COMPOSITION AND METHOD FOR PRODUCING MICROLENS

TECHNICAL FIELD

The present invention relates to a positive resist composition containing a triazine skeleton-having multifunctional epoxy compound as a crosslinker. This composition is particularly suitable for using as a planarizing film and a microlens material.

BACKGROUND ART

A microlens for an image sensor such as a charge coupled device (CCD) can produce a high-definition image sensor mainly by forming a fine pattern and the fine pattern is produced using a photoresist. Specifically, a microlens is produced by a method including: applying a resist composition containing a polymer resin and a photosensitizer on a substrate to make a film of the resist composition; patterning the resultant film by a photolithography method; and developing the film to form one pattern. Therefore, for the resist composition used as a microlens material, it is required to be highly sensitive and excellent in pattern forming ability. The formed lens pattern is exposed to a high temperature condition in a soldering process, so that for the resist composition, it is also required that the formed lens pattern has a desired curvature radius and has high heat resistance and high transparency.

As one of important characteristics among the above required characteristics, the sensitivity can be mentioned. The enhancement of the sensitivity leads to shortening of the production time in the industrial production and at the present when the demand for the image sensor is substantially increasing in recent years, the sensitivity has become one of extremely important characteristics. When the sensitivity is not satisfactory, a desired pattern cannot be resolved, so that it becomes impossible to form an advantageous lens shape. Although the sensitivity can be enhanced also by enhancing the solubility of a polymer in the material in an alkaline developer, when the composition of the polymer is changed, it influences largely on other characteristics such as a refractive index and hygroscopicity, so that there is a limitation.

As the important characteristics required for the microlens material besides the sensitivity, transparency and heat resistance can be mentioned. Usually, a module such as a camera having a microlens is mounted on a substrate in which an electronic circuit has already been provided. Although for this mounting, a lead-containing solder has conventionally been used, lead is harmful for the human body and the environment, so that in recent years, the use of a lead-free solder containing no lead is advocated. The lead-free solder using a metal other than lead has a melting point higher than that of the lead-containing solder. Therefore, when in the mounting process, a lead-free solder is used, there becomes required a heating treatment at a temperature higher than in the case of using a lead-containing solder. At this time, there is caused the problem that when a microlens is produced with a material having unsatisfactory heat resistance, transparency of the microlens is lowered. Then, in order to obtain a resist composition (microlens material) having high heat resistance, it is required with respect to not only the used resin, but also the used crosslinkable compound, sensitizer, and other additives to be excellent in heat resistance.

SUMMARY OF THE INVENTION

Problem to be Solved by the Invention

As described above, in such a situation that as the microlens material, a resist composition satisfying various characteristics is required, particularly there are many crosslinkable compounds having unsatisfactory resistance to yellowing by heat, which becomes a cause to lower the heat resistance of the resist composition.

Although, for example, as the crosslinkable compound, there is disclosed epoxy compounds (see Patent Documents 1, 2, and 3) having a long chain alkylene chain as a compound having a triazine-trione ring having high heat resistance and a long chain alkylene chain having a solubility, there is no disclosure for applying such a compound capable of expecting high heat resistance to the resist composition.

Thus, the conventionally disclosed resist compositions are not a resist composition capable of satisfying various performances such as having satisfactory heat resistance while having high sensitivity.

Accordingly, it is an object of the present invention to provide a resist composition suitable for forming a microlens which is excellent in transparency, heat resistance, and sensitivity characteristics, excellent in solubility in a developer, and as the result thereof has high resolution.

Means for Solving the Problem

As a result of assiduous research intended to overcome these disadvantages, the inventors of the present invention have found that by adopting a specific multifunctional epoxy compound having a triazine skeleton as a crosslinkable compound in a resist composition, the composition becomes a material excellent in heat resistance and transparency and having high sensitivity, and have completed the present invention.

That is, according to a first aspect, the present invention relates to a positive resist composition containing:

a component (A): an alkali-soluble polymer;

a component (B): a compound having an organic group to be photolyzed to generate an alkali-soluble group;

a component (C): a crosslinkable compound of Formula (1):

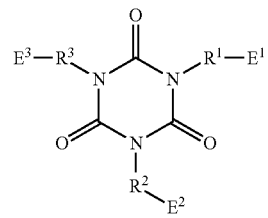

Formula (1)

[where $R^1$, $R^2$, and $R^3$ are independently a $C_{1-6}$ alkylene group or oxyalkylene group which are optionally branched; and $E^1$, $E^2$, $E^3$ are independently a group containing a structure of Formula (2) or Formula (3):

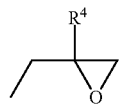

Formula (2)

Formula (3)

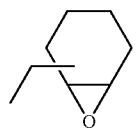

(where $R^4$ is a hydrogen atom or a methyl group)]; and a component (D): a solvent.

According to a second aspect, the present invention relates to the positive resist composition according to the first aspect, in which the alkali-soluble polymer as the component (A) is a polymer containing in a repeating unit thereof, a hydroxy group, a carboxy group, or a combination thereof.

According to a third aspect, the present invention relates to the positive resist composition according to the first aspect or the second aspect, in which the alkali-soluble polymer as the component (A) is a copolymer of a monomer having a hydroxy group, a carboxy group, or a combination thereof with a monomer having a hydrophobic group.

According to a fourth aspect, the present invention relates to the positive resist composition according to any one of the first aspect to the third aspect, in which the component (B) is a compound having a structure of Formula (4):

Formula (4)

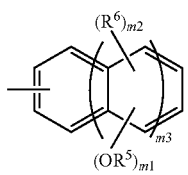

[where $R^5$ is a hydrogen atom or a structure of Formula (5):

Formula (5)

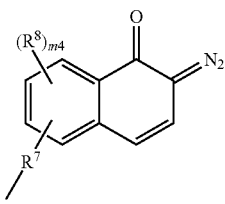

(where $R^7$ is a single bond or a $—SO_3—$ group; $R^8$ is a $C_{1-10}$ alkyl group; and m4 is an integer of 0 to 3); $R^6$ is a $C_{1-10}$ substituted or unsubstituted alkyl group, a halogen atom, or a $C_{1-10}$ alkoxy group; m3 is an integer of 0 or 1, where when m3 is 0, m1 is an integer of 1 to 5 and m2 is an integer satisfying $0 \le m2 \le (5-m1)$, and when m3 is 1, m1 is an integer of 1 to 7 and m2 is an integer satisfying $0 \le m2 \le (7-m1)$; with the proviso that $R^5$ is a structure of Formula (5) in an amount of 10 to 100% by mol, based on the total number of moles of the substituent $R^5$ contained in the compound having a structure of Formula (4)].

According to a fifth aspect, the present invention relates to the positive resist composition according to the fourth aspect, in which the component (B) is a compound of Formula (6):

Formula (6)

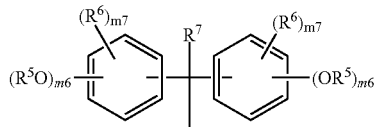
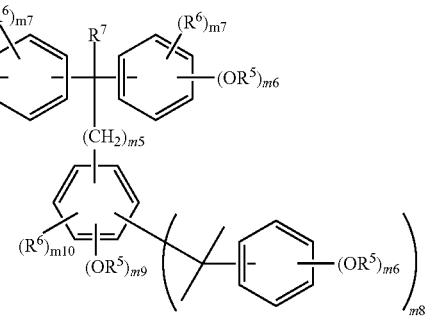

(where $R^5$ and $R^6$ are the same group as those defined in the above Formula (4); $R^7$ is a hydrogen atom or a $C_{1-10}$ alkyl group; m5 is an integer of 0 to 10; m6 is an integer of 1 to 5; m7 is an integer satisfying $0 \le m7 \le (5-m6)$; m8 is an integer of 0 to 1; m9 is an integer of 0 to 5; m10 is an integer satisfying $0 \le m10 \le (5-m8-m9)$; with the proviso that $R^5$ is a structure of Formula (5) in an amount of 10 to 100% by mol, based on the total number of moles of the substituent $R^5$ contained in the compound of Formula (6)).

According to a sixth aspect, the present invention relates to the positive resist composition according to any one of the first aspect to the fifth aspect, in which in the crosslinkable compound as the component (C), $E^1$, $E^2$, $F^3$, or two or more types selected from $E^1$ to $F^3$ in Formula (1) is (are) a group having an organic group of Formula (7):

Formula (7)

(where $R^4$ is a hydrogen atom or a methyl group).

According to a seventh aspect, the present invention relates to the positive resist composition according to any one of the first aspect to the sixth aspect, in which the positive resist composition, when formed into a composition film having a thickness of 1.0 μm, has a coating film physical property of 80% or more that is a transmittance relative to light having a wavelength of 400 to 730 nm.

According to an eighth aspect, the present invention relates to a pattern forming method including: applying the positive resist composition described in any one of the first aspect to the sixth aspect on a substrate; and subjecting the resultant coating to drying, exposure, and development.

According to a ninth aspect, the present invention relates to the pattern forming method according to the eighth aspect, including a heating process after exposure and before development.

According to a tenth aspect, the present invention relates to a solid-state image sensor containing a microlens or a planarizing film produced by the pattern forming method described in the eighth aspect or the ninth aspect.

Effects of the Invention

With respect to the positive resist composition of the present invention, by using as a crosslinker, a multifunctional epoxy compound having a triazine-trione ring skeleton, a coating film obtained using the composition has high sensitivity and is excellent in solubility in a developer and a cured film obtained from the coating film can be obtained as a cured film having high transparency and high heat resistance and being excellent also in solvent resistance. Particularly, a cured film having a film thickness of 1.0 µm which is obtained according to the present invention has excellent transparency such as a transmittance at a wavelength of 400 to 730 nm of 80% or more.

Therefore, the positive resist composition of the present invention can preferably be used as a material for a microlens and a planarizing film material for forming a microlens.

MODES FOR CARRYING OUT THE INVENTION

The present invention targets a composition suitable for a planarizing film or a microlens material.

As one application to which a microlens is applied, there can be mentioned an image sensor which is a semiconductor device for converting an optical image into an electric signal. The image sensor is constituted with a photodiode (light sensing element) for sensing an irradiated light and a part for converting the irradiated light into an electric signal. The larger the light income of a photodiode is, the higher the sensitivity of an image sensor relative to light is. As one of the collimation techniques for enhancing the light income, the above forming method of a microlens is adopted. Specifically, in an upper part of a photodiode, a convex microlens is produced with a substance having a high light transmittance and by the microlens, the path of an incident light is refracted to collect a large amount of light on the photodiode. More in detail, on a photodiode formed on a substrate, an interlayer insulation layer is formed and thereon, a protective film is formed, followed by forming a color filter layer composed of R/G/B on the protective film. Further, on the color filter, a planarizing film is formed and thereon, a microlens is formed. Thus, for the microlens material, high transparency as an optical material is required.

Conventionally, for forming the microlens, a positive photosensitive material (resist material) is used. Specifically, by applying a positive resist composition on a planarizing layer and by drying the resultant coating, a positive resist layer is formed and by exposure and development, a positive resist pattern is formed, followed by forming a convex microlens by a heat reflow or the like. The shape of the lens depends on the pattern shape after development and then, the factor with respect to the lens shape such as the curvature and the height of the formed lens affects the collection efficiency. Therefore, for the microlens material, it is also required to be able to form an arbitral lens shape with considering the focus of a converged light, that is, to have advantageous sensitivity and advantageous patterning property.

A planarizing film layer existing as an underlayer of the microlens also plays an important role for the formation of a homogeneous optical axis of the microlens by forming a homogeneous surface of the planarizing film layer and for enhancing the collection efficiency to the photodiode higher, a planarizing film layer having high transparency is also required. There is also the case where for wiring, an opening is provided in the planarizing film layer, so that it is desired that the planarizing film layer has advantageous patterning property.

The present invention is invented for providing a positive resist composition which is a material possessing the above performances required for the microlens and the planarizing film and hereinafter, each component contained in the composition will be described in detail.

The present invention is a positive resist composition containing
the component (A): an alkali-soluble polymer,
the component (B): a compound having an organic group to be photolyzed to generate an alkali-soluble group,
the component (C): a crosslinkable compound of Formula (1), and
the compound (D): a solvent.

In Formula (1), $R^1$, $R^2$, and, $R^3$ are independently a $C_{1-6}$ alkylene group or oxyalkylene group which may be branched, and $E^1$, $E^2$, and $E^3$ are independently a group containing a structure of Formula (2) or Formula (3).

The positive resist composition of the present invention may further contain, if necessary, the below-described component (E): a surfactant and/or component (F): an adhesion accelerator.

In the positive resist composition of the present invention, the solid content is 3 to 50% by mass, preferably 5 to 35% by mass, further preferably 7 to 30% by mass. The solid content means the content of a component remaining after subtracting a solvent from the positive resist composition.

In the above solid content, the content of the component (A) is 8 to 90% by mass, preferably 40 to 90% by mass, further preferably 50 to 80% by mass.

In the solid content, the content of the component (B) is 1 to 90% by mass, preferably 5 to 50% by mass, further preferably 10 to 30% by mass. When the content of the component (B) is this lower limit value or less, the difference in the solubility in a developer between an exposed portion and an unexposed portion becomes small, so that patterning by the development may become difficult. When the content of the component (B) is more than the upper limit value, by exposure for a short time, the component (B) (for example, a 1,2-naphthoquinone diazide compound) is not satisfactorily decomposed, so that the sensitivity of the microlens may be lowered or the component (B) may absorb light and consequently, transparency of a cured film may be lowered.

In the solid content, the content of the component (C) is 0.24 to 45% by mass, preferably 0.56 to 40% by mass, 0.80 to 35% by mass. When the content of the crosslinkable compound is small, the density of the crosslinkage formed by the crosslinkable compound is not satisfactory, so that the effect of enhancing process resistance such as heat resistance, solvent resistance, and long-period baking resistance after the pattern formation cannot satisfactorily be obtained according to the object of the use. On the other hand, when the content of the crosslinkable compound is more than the above value range, according to the object of the use, an uncrosslinked crosslinkable compound exists and it may be caused that the resolution is lowered, or process resistance such as heat resistance, solvent resistance, and long-period baking resistance after the pattern formation are lowered, or the preservation stability of the resist composition becomes impaired.

Hereinafter, each component will be described in detail.

[Component (A): Alkali-Soluble Polymer]

As the alkali-soluble polymer as the component (A), there can be used a polymer containing a hydroxy group, a carboxy group, or a combination thereof, that is, a polymer containing in a repeating unit thereof, a hydroxy group and a carboxy group.

For example, as the monomer constituting the above polymer, a hydroxy group-containing monomer, a carboxy group-containing monomer, and a monomer containing the both groups can be used, and a polymer obtained by using these monomers individually or a copolymer obtained by using these monomers in combination with other copolymerizable monomers can be used as the alkali-soluble polymer.

Examples of the monomer having a carboxy group constituting the alkali-soluble polymer as the component (A) include: monocarboxylic acids such as acrylic acid, methacrylic acid, crotonic acid, and 4-vinylbenzoic acid; dicarboxylic acids such as maleic acid, fumaric acid, citraconic acid, mesaconic acid, and itaconic acid; and dicarboxylic anhydrides. When these monomers having a carboxy group are copolymerized with other copolymerizable monomers, the content of the monomer having a carboxy group is preferably 10 to 70% by mass, particularly preferably 10 to 50% by mass, based on the total mass of all monomers used for the copolymerization, to be used. When the used amount of the monomer having a carboxy group is less than 10% by mass, developing property of the positive resist composition after the exposure thereof may be lowered. On the other hand, when the used amount thereof is more than 70% by mass, a predetermined percentage residual film may not be obtained.

Examples of the monomer having a hydroxy group constituting the alkali-soluble polymer as the component (A) include monomers having a phenolic hydroxy group such as 4-hydroxystyrene and 4-hydroxyphenyl methacrylate. When these monomers having a hydroxy group are copolymerized with other copolymerizable monomers, the content of the monomer having a hydroxy group is preferably 30 to 100% by mass, particularly preferably 50 to 100% by mass, based on the total mass of all monomers used for the copolymerization, to be used. When the used amount of the monomer having a hydroxy group is less than 30% by mass, developing property of the alkali-soluble polymer tends to be lowered.

When the alkali-soluble polymer as the component (A) is a copolymer of the above monomer having a carboxy group, a hydroxy group, or a combination thereof with another copolymerizable monomer, as the other copolymerizable monomer, a monomer having a hydrophobic group can be used. Examples of the monomer having a hydrophobic group used here include: methacrylic acid alkyl esters such as methyl methacrylate, ethyl methacrylate, n-butyl methacrylate, sec-butyl methacrylate, and tert-butyl methacrylate; cyclic ethers having an unsaturated double bond such as glycidyl acrylate, glycidyl methacrylate, glycidyl α-ethylacrylate, glycidyl α-n-propylacrylate, glycidyl α-n-butylacrylate, 3,4-epoxybutyl acrylate, 3,4-epoxybutyl methacrylate, 6,7-epoxyheptyl acrylate, 6,7-epoxyheptyl methacrylate, 6,7-epoxyheptyl α-ethylacrylate, o-vinylbenzyl glycidyl ether, m-vinylbenzyl glycidyl ether, p-vinylbenzyl glycidyl ether, β-methylglycidyl (meth)acrylate, β-ethylglycidyl (meth)acrylate, β-propylglycidyl (meth)acrylate, β-methylglycidyl α-thylacrylate, 3-methyl-3,4-epoxybutyl (meth)acrylate, 3-ethyl-3,4-epoxybutyl (meth)acrylate, 4-methyl-4,5-epoxypentyl (meth)acrylate, 5-methyl-5,6-epoxyhexyl (meth)acrylate, 3-ethyl-3-oxetanyl methacrylate, and 3-ethyl-3-oxetanyl acrylate; acrylic acid alkyl esters such as methyl acrylate and isopropyl acrylate; methacrylic acid cyclic alkyl esters such as cyclohexyl methacrylate, 2-methylcyclohexyl methacrylate, dicyclopentanyl methacrylate, dicyclopentanyloxyethyl methacrylate, and isobornyl methacrylate; acrylic acid cyclic alkyl esters such as cyclohexyl acrylate, 2-methylcyclohexyl acrylate, dicyclopentanyl acrylate, dicyclopentanyloxyethyl acrylate, and isobornyl acrylate; N-substituted maleimide such as N-cyclohexylmaleimide, N-phenylmaleimide, and N-benzylmaleimide; methacrylic acid aryl esters such as phenyl methacrylate and benzyl methacrylate; acrylic acid aryl esters such as phenyl acrylate and benzyl acrylate; dicarboxylic acid diesters such as diethyl maleate, diethyl fumarate, and diethyl itaconate; hydroxyalkyl esters such as 2-hydroxyethyl methacrylate and 2-hydroxypropyl methacrylate; styrene; α-methylstyrene; m-methylstyrene; p-methylstyrene; vinyltoluene; p-methoxystyrene; 2-vinylnaphthalene; 4-binylbiphenyl; acrylonitrile; methacrylonitrile; vinyl chloride; vinylidene chloride; acrylamide; methacrylamide; vinyl acetate; 1,3-butadiene; isoprene; 2,3-dimethyl-1,3-butadiene; phenylmaleimide; ethylene glycol diacrylate; diethylene glycol diacrylate; triethylene glycol diacrylate; neopentyl glycol diacrylate; glycerol diacrylate; ethylene glycol dimethacrylate; diethylene glycol dimethacrylate; triethylene glycol dimethacrylate; neopentyl glycol dimethacrylate; and glycerol dimethacrylate.

Among them, preferred are styrene, tert-butyl methacrylate, dicyclopentanyl methacrylate, p-methoxystyrene, 2-methylcyclohexyl acrylate, N-cyclohexylmaleimide, N-phenylmaleimide, 1,3-butadiene, ethylene glycol dimethacrylate, diethylene glycol dimethacrylate, glycol dimethacrylate, glycidyl methacrylate, β-methylglycidyl methacrylate, 3-ethyl-3-oxetanyl methacrylate, 2-vinylnaphthalene, and 4-vinylbiphenyl, in terms of the copolymerization reactivity, controlling property of the molecular weight distribution, and the solubility in an alkaline aqueous solution. These monomers may be used individually or in combination.

Specific examples of the solvent used for the synthesis of the alkali-soluble polymer as the component (A) include: alcohols such as methanol and ethanol; ethers such as tetrahydrofuran; glycol ethers such as ethylene glycol monomethyl ether and ethylene glycol monoethyl ether; ethylene glycol alkyl ether acetates such as methyl cellosolve acetate and ethyl cellosolve acetate; diethylene glycols such as diethylene glycol monomethyl ether, diethylene glycol monoethyl ether, diethylene glycol dimethyl ether, diethylene glycol diethyl ether, and diethylene glycol ethylmethyl ether; propylene glycol monoalkyl ethers such as propylene glycol methyl ether, propylene glycol ethyl ether, propylene glycol propyl ether, propylene glycol butyl ether; propylene glycol alkyl ether acetates such as propylene glycol methyl ether acetate, propylene glycol ethyl ether acetate, propylene glycol propyl ether acetate, and propylene glycol butyl ether acetate; propylene glycol alkyl ether acetates such as propylene glycol methyl ether propionate, propylene glycol ethyl ether propionate, propylene glycol propyl ether propionate, and propylene glycol butyl ether propionate; aromatic hydrocarbons such as toluene and xylene; ketones such as methyl ethyl ketone, cyclohexanone, and 4-hydroxy-4-methyl-2-pentanone; and esters such as methyl acetate, ethyl acetate, propyl acetate, butyl acetate, ethyl 2-hydroxypropionate, methyl 2-hydroxy-2-methylpropionate, ethyl 2-hydroxy-2-methylpropionate, methyl hydroxyacetate, ethyl hydroxyacetate, butyl hydroxyacetate, methyl lactate, ethyl lactate, propyl lactate, butyl lactate, methyl 3-hydroxypropionate, ethyl 3-hydroxypropionate, propyl 3-hydroxypropionate, butyl 3-hydroxypropionate, methyl 2-hydroxy-3-methylbutanoate, methyl methoxyacetate, ethyl methoxyacetate, propyl methoxyacetate, butyl methoxyacetate, methyl ethoxyacetate, ethyl ethoxyacetate, propyl ethoxyacetate, butyl ethoxyacetate, methyl propoxyacetate, ethyl propoxyacetate, propyl propoxyacetate, butyl propoxyacetate, methyl butoxyacetate, ethyl butoxyacetate, propyl butoxyacetate, butyl butoxyacetate, methyl 2-methoxypropionate, ethyl 2-methoxypropionate, propyl 2-methoxypropionate, butyl 2-methoxypropionate, methyl 2-ethoxypropionate, ethyl 2-ethoxypropionate, propyl 2-ethoxypropionate, butyl 2-ethoxypropionate, methyl 2-butoxypropionate, ethyl 2-butoxypropionate, propyl 2-butoxypropionate, butyl 2-butoxypropionate, methyl 3-methoxypropionate, ethyl 3-methoxypropionate, propyl 3-methoxypropionate, butyl 3-methoxypropionate, methyl 3-ethoxypropionate, ethyl 3-ethoxypropionate, propyl 3-ethoxypropionate, butyl 3-ethoxypropionate, methyl 3-propoxypropionate, ethyl 3-propoxypropionate, propyl 3-propoxypropionate, butyl 3-propoxypropionate, methyl 3-butoxypropionate, ethyl 3-butoxypropionate, propyl 3-butoxypropionate, and butyl 3-butoxypropionate. These solvents can be used as the solvent (D) of the positive resist composition of the present invention.

As the polymerization initiator used for the synthesis of the alkali-soluble polymer as the component (A), a polymerization initiator generally known as a radical polymerization initiator can be used and examples thereof include an azo compound such as 2,2'-azobisisobutyronitrile, 2,2'-azobis-(2,4-dimethylvaleronitrile), and 2,2'-azobis-(4-methoxy-2,4-dimethylvaleronitrile); an organic peroxide such as benzoyl peroxide, lauroyl peroxide, tert-butylperoxypivalate, and 1,1'-bis-(tert-butylperoxy)cyclohexane; and hydrogen peroxide. When as the radical polymerization initiator, a peroxide is used, the peroxide may be used in combination with a reductant as a redox-type polymerization initiator.

In the synthesis of the alkali-soluble polymer as the component (A), a molecular weight controlling agent may be used for controlling the molecular weight. Specific examples of the molecular weight controlling agent include: halogenated hydrocarbons such as chloroform and carbon tetrachloride; mercaptans such as n-hexylmercaptan, n-octylmercaptan, n-dodecylmercaptan, tert-dodecylmercaptan, and thioglycolic acid; xanthogens such as dimethylxanthogen sulfide and diisopropylxanthogen disulfide; terpineol; and α-methylstyrene dimer.

The alkali-soluble polymer as the component (A) used in the present invention has desirably a weight average molecular weight (hereinafter, called as "Mw") in terms of polystyrene of usually $2 \times 10^3$ to $1 \times 10^5$, preferably $5 \times 10^3$ to $5 \times 10^4$. When Mw is less than $2 \times 10^3$, developing property, percentage residual film, and the like of the obtained coating film may be lowered or the coating film may be poor in pattern shape, heat resistance, or the like. On the other hand, when Mw is more than $1 \times 10^5$, the sensitivity of the coating film may be lowered or the coating film may be poor in pattern shape.

As described above, the alkali-soluble polymer as the component (A) in the present invention is a polymer containing a hydroxy group and/or a carboxy group and has an appropriate solubility in an alkali aqueous solution. The positive resist composition of the present invention containing such a component (A) can easily form a coating film having a predetermined pattern without causing developing failure during the development thereof and without causing a film loss.

[Component (B): A Compound Having an Organic Group to be Photolyzed to Generate an Alkali-Soluble Group]

The component (B) is a compound having an organic group to be photolyzed to generate an alkali-soluble group and specifically, as the component (B), a 1,2-naphthoquinone diazide compound having a partial structure of Formula (4) can be used.

When a coating film formed from the positive resist composition of the present invention is subjected to exposure and development using a photomask, a 1,2-naphthoquinone diazide group contained in the component (B) existing in an exposed portion is converted into ketene by being irradiated with light. The resultant ketene has high reactivity, so that the ketene is contacted with a water content to generate a carboxy group. That is, in the exposed portion, a 1,2-naphthoquinone diazide group generates indene carboxylic acid by exposure, so that the resist composition becomes soluble in a developer, so that by the difference in the solubility in a developer between the exposed portion and the unexposed portion, a pattern can be formed.

In Formula (4), $R^5$ is a hydrogen atom or a structure of Formula (5). $R^6$ is a $C_{1-10}$ substituted or unsubstituted alkyl group, a halogen atom, or a $C_{1-10}$ alkoxy group. m3 is an integer of 0 or 1. When m3 is 0, m1 is an integer of 1 to 5 and m2 is an integer satisfying 0≤m2≤(5−m1), and when m3 is 1, m1 is an integer of 1 to 7 and m2 is an integer satisfying 0≤m2≤(7−m1).

However, $R^5$ is a structure of Formula (5) in an amount of 10 to 100% by mol. That is, it is indicated that 10 to 100% by mol of the substituent $R^5$ is a structure of Formula (5), based on the total number of moles of the substituent $R^5$ contained in the compound having a structure of Formula (4).

In Formula (5): $R^7$ is a single bond or a —$SO_3$— group; $R^8$ is a $C_{1-10}$ alkyl group; and m4 is an integer of 0 to 3.

Examples of the $C_{1-10}$ alkyl group include methyl, ethyl, n-propyl, isopropyl, cyclopropyl, n-butyl, isobutyl, sec-butyl, tert-butyl, cyclobutyl, 1-methyl-cyclopropyl, 2-methyl-cyclopropyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, cyclopentyl, 1-methyl-cyclobutyl, 2-methyl-cyclobutyl, 3-methyl-cyclobutyl, 1,2-dimethyl-cyclopropyl, 2,3-dimethyl-cyclopropyl, 1-ethyl-cyclopropyl, 2-ethyl-cyclopropyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, cyclohexyl, 1-methyl-cyclopentyl, 2-methyl-cyclopentyl, 3-methyl-cyclopentyl, 1-ethyl-cyclobutyl, 2-ethyl-cyclobutyl, 3-ethyl-cyclobutyl, 1,2-dimethyl-cyclobutyl, 1,3-dimethyl-cyclobutyl, 2,2-dimethyl-cyclobutyl, 2,3-dimethyl-cyclobutyl, 2,4-dimethyl-cyclobutyl, 3,3-dimethyl-cyclobutyl, 1-n-propyl-cyclopropyl, 2-n-propyl-cyclopropyl, 1-isopropyl-cyclopropyl, 2-isopropyl-cyclopropyl, 1,2,2-trimethyl-cyclopropyl, 1,2,3-trimethyl-cyclopropyl, 2,2,3-trimethyl-cyclopropyl, 1-ethyl-2-methyl-cyclopropyl, 2-ethyl-1-methyl-cyclopropyl, 2-ethyl-2-methyl-cyclopropyl, and 2-ethyl-3-methyl-cyclopropyl.

Examples of the halogen atom include a fluorine atom, a chlorine atom, a bromine atom, and an iodine atom.

Examples of the $C_{1-10}$ alkoxy group include methoxy, ethoxy, n-propoxy, isopropoxy, n-butoxy, isobutoxy, sec-butoxy, tert-butoxy, n-pentoxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, and 1-ethyl-2-methyl-n-propoxy.

As the component (B), specifically, a compound of Formula (6) can be used. In Formula (6): $R^5$ and $R^6$ are the same group as those defined in Formula (4); $R^7$ is a hydrogen atom or a $C_{1-10}$ alkyl group; m5 is an integer of 0 to 10; m6 is an integer of 1 to 5; m7 is an integer satisfying 0≤m7≤(5−m6); m8 is an integer of 0 to 1; m9 is an integer of 0 to 5; and m10 is an integer satisfying 0≤m10≤(5−m8−m9).

However, $R^5$ is a structure of Formula (5) in an amount of 10 to 100% by mol. That is, it is indicated that 10 to 100% by mol of the substituent $R^5$ is a structure of Formula (5), based on the total number of moles of the substituent $R^5$ contained in the compound of Formula (6).

Specific examples of the component (B) include compounds of Formulae (B-1) to (B-5):

Formula (B-1)
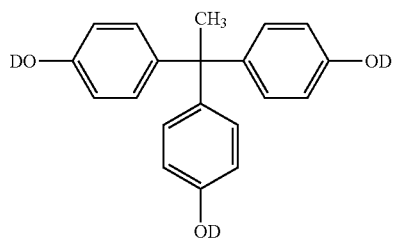

Formula (B-2)
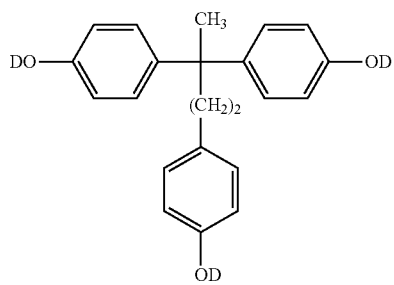

Formula (B-3)
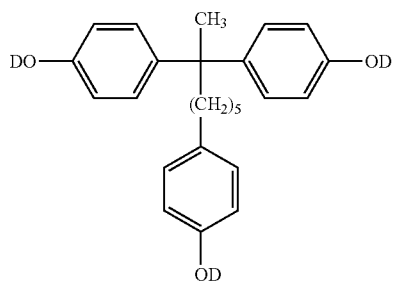

Formula (B-4)
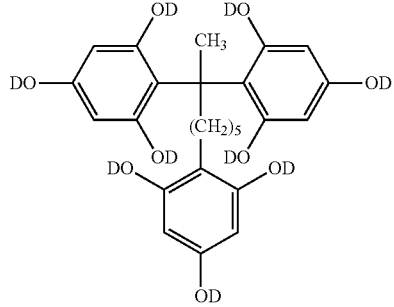

Formula (B-5)
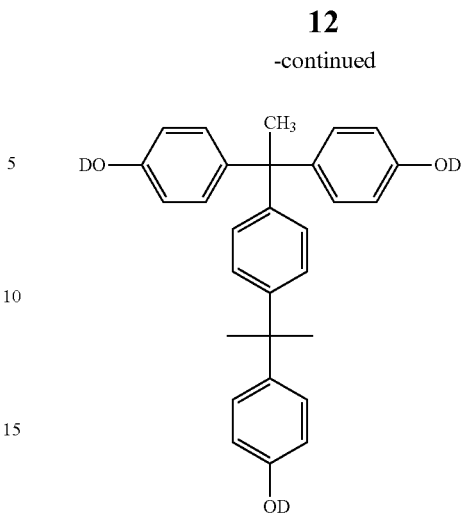

(in Formulae (B-1)-(B-5), D is a hydrogen atom or a 1,2-naphthoquinone diazide group of Formula (5)).

Examples of the component (B) used in the present invention include also compounds of Formula (B-6) to Formula (B-10):

Formula (B-6)
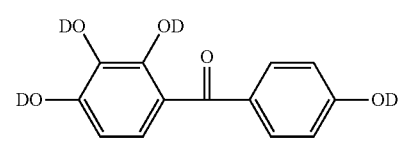

Formula (B-7)
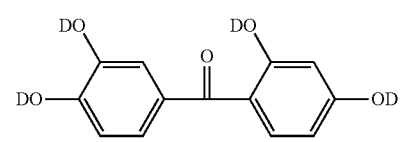

Formula (B-8)
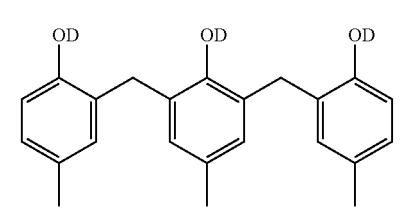

Formula (B-9)
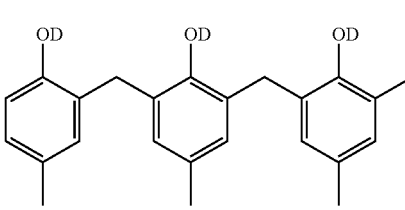

Formula (B-10)
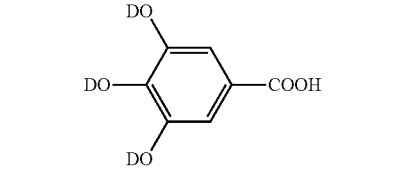

(in Formulae (B-6)-(B-10), D is a hydrogen atom or a 1,2-naphthoquinone diazide group of Formula (5)).

[Component (C): A Crosslinkable Compound of Formula (1)]

As the component (C) used in the present invention, a crosslinkable compound of Formula (1) can be used.

In Formula (1), $R^1$, $R^2$, and, $R^3$ are independently a $C_{1-6}$ alkylene group or oxyalkylene group which may be branched.

$E^1$, $E^2$, and $E^3$ are independently a group containing a structure of Formula (2) or Formula (3). In Formula (2), $R^4$ is a hydrogen atom or a methyl group.

Examples of the $C_{1-6}$ alkylene group include methylene, ethylene, n-propylene, isopropylene, cyclopropylene, n-butylene, isobutylene, sec-butylene, tert-butylene, cyclobutylene, 1-methyl-cyclopropylene, 2-methyl-cyclopropylene, n-pentylene, 1-methyl-n-butylene, 2-methyl-n-butylene, 3-methyl-n-butylene, 1,1-dimethyl-n-propylene, 1,2-dimethyl-n-propylene, 2,2-dimethyl-n-propylene, 1-ethyl-n-propylene, cyclopentylene, 1-methyl-cyclobutylene, 2-methyl-cyclobutylene, 3-methyl-cyclobutylene, 1,2-dimethyl-cyclopropylene, 2,3-dimethyl-cyclopropylene, 1-ethyl-cyclopropylene, 2-ethyl-cyclopropylene, n-hexylene, 1-methyl-n-pentylene, 2-methyl-n-pentylene, 3-methyl-n-pentylene, 4-methyl-n-pentylene, 1,1-dimethyl-n-butylene, 1,2-dimethyl-n-butylene, 1,3-dimethyl-n-butylene, 2,2-dimethyl-n-butylene, 2,3-dimethyl-n-butylene, 3,3-dimethyl-n-butylene, 1-ethyl-n-butylene, 2-ethyl-n-butylene, 1,1,2-trimethyl-n-propylene, 1,2,2-trimethyl-n-propylene, 1-ethyl-1-methyl-n-propylene, 1-ethyl-2-methyl-n-propylene, cyclohexylene, 1-methyl-cyclopentylene, 2-methyl-cyclopentylene, 3-methyl-cyclopentylene, 1-ethyl-cyclobutylene, 2-ethyl-cyclobutylene, 3-ethyl-cyclobutylene, 1,2-dimethyl-cyclobutylene, 1,3-dimethyl-cyclobutylene, 2,2-dimethyl-cyclobutylene, 2,3-dimethyl-cyclobutylene, 2,4-dimethyl-cyclobutylene, 3,3-dimethyl-cyclobutylene, 1-n-propyl-cyclopropylene, 2-n-propyl-cyclopropylene, 1-isopropyl-cyclopropylene, 2-isopropyl-cyclopropylene, 1,2,2-trimethyl-cyclopropylene, 1,2,3-trimethyl-cyclopropylene, 2,2,3-trimethyl-cyclopropylene, 1-ethyl-2-methyl-cyclopropylene, 2-ethyl-1-methyl-cyclopropylene, 2-ethyl-2-methyl-cyclopropylene, and 2-ethyl-3-methyl-cyclopropylene. $R^1$, $R^2$, and $R^3$ individually are preferably a $C_{1-3}$ alkylene group among the above-exemplified groups, particularly preferably the above $C_{2-3}$ alkylene groups.

Examples of the $C_{1-6}$ oxyalkylene group include oxymethylene, oxyethylene, oxy-n-propylene, oxyisopropylene, oxycyclopropylene, oxy-n-butylene, oxyisobutylene, oxy-sec-butylene, oxy-tert-butylene, oxycyclobutylene, oxy-1-methyl-cyclopropylene, oxy-2-methyl-cyclopropylene, oxy-n-pentylene, oxy-1-methyl-n-butylene, oxy-2-methyl-n-butylene, oxy-3-methyl-n-butylene, oxy-1,1-dimethyl-n-propylene, oxy-1,2-dimethyl-n-propylene, oxy-2,2-dimethyl-n-propylene, oxy-1-ethyl-n-propylene, oxycyclopentylene, oxy-1-methyl-cyclobutylene, oxy-2-methyl-cyclobutylene, oxy-3-methyl-cyclobutylene, oxy-1,2-dimethyl-cyclopropylene, oxy-2,3-dimethyl-cyclopropylene, oxy-1-ethyl-cyclopropylene, oxy-2-ethyl-cyclopropylene, oxy-n-hexylene, oxy-1-methyl-n-pentylene, oxy-2-methyl-n-pentylene, oxy-3-methyl-n-pentylene, oxy-4-methyl-n-pentylene, oxy-1,1-dimethyl-n-butylene, oxy-1,2-dimethyl-n-butylene, oxy-1,3-dimethyl-n-butylerie, oxy-2,2-dimethyl-n-butylene, oxy-2,3-dimethyl-n-butylene, oxy-3,3-dimethyl-n-butylene, oxy-1-ethyl-n-butylene, oxy-2-ethyl-n-butylene, oxy-1,1,2-trimethyl-n-propylene, oxy-1,2,2-trimethyl-n-propylene, oxy-1-ethyl-1-methyl-n-propylene, oxy-1-ethyl-2-methyl-n-propylene, oxycyclohexylene, oxy-1-methyl-cyclopentylene, oxy-2-methyl-cyclopentylene, oxy-3-methyl-cyclopentylene, oxy-1-ethyl-cyclobutylene, oxy-2-ethyl-cyclobutylene, oxy-3-ethyl-cyclobutylene, oxy-1,2-dimethyl-cyclobutylene, oxy-1,3-dimethyl-cyclobutylene, oxy-2,2-dimethyl-cyclobutylene, oxy-2,3-dimethyl-cyclobutylene, oxy-2,4-dimethyl-cyclobutylene, oxy-3,3-dimethyl-cyclobutylene, oxy-1-n-propyl-cyclopropylene, oxy-2-n-propyl-cyclopropylene, oxy-1-isopropyl-cyclopropylene, oxy-2-isopropyl-cyclopropylene, oxy-1,2,2-trimethyl-cyclopropylene, oxy-1,2,3-trimethyl-cyclopropylene, oxy-2,2,3-trimethyl-cyclopropylene, oxy-1-ethyl-2-methyl-cyclopropylene, oxy-2-ethyl-1-methyl-cyclopropylene, oxy-2-ethyl-2-methyl-cyclopropylene, and oxy-2-ethyl-3-methyl-cyclopropylene. Particularly, an oxyethylene group and an oxyisopropylene group are preferably used.

The component (C) is preferably a compound in which in Formula (1): $R^1$, $R^2$, and, $R^3$ are a $C_{1-3}$ alkylene group, preferably a $C_{2-3}$ alkylene group; $E^1$, $E^2$, and $E^3$ are an organic group of Formula (2); and $R^4$ is a hydrogen atom.

As the crosslinkable compound as the component (C), there can also be used a compound in which $E^1$, $E^2$, $E^3$, or two or more types selected from $E^1$ to $E^3$ in Formula (1) has (have) an organic group of Formula (7):

Formula (7)

(where $R^4$ is a hydrogen atom or a methyl group). For example, as such a compound, there can be used a crosslinkable compound of Formula (1) in which the content of an organic group of Formula (2) is 67 to 100% by mol, preferably 90 to 100% by mol, based on the total number of moles of $E^1$, $E^2$, and $E^3$, and the residual content is the content of an organic group of Formula (7).

As the component (C) in the present invention, there can be preferably used, for example, compounds of Formula (C-1-1) to Formula (C-1-15):

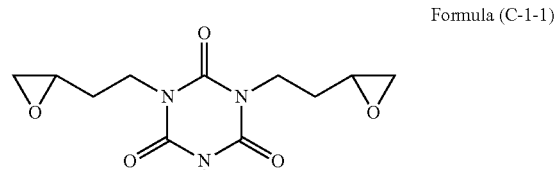

Formula (C-1-1)

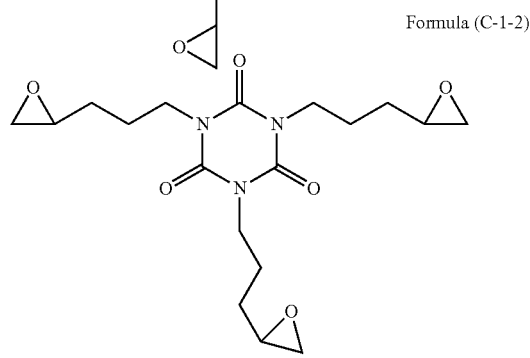

Formula (C-1-2)

-continued
Formula (C-1-3)
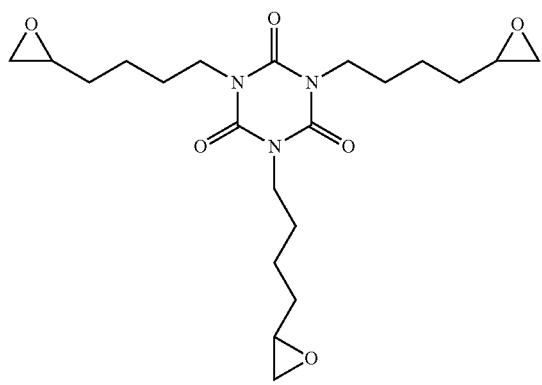
Formula (C-1-4)
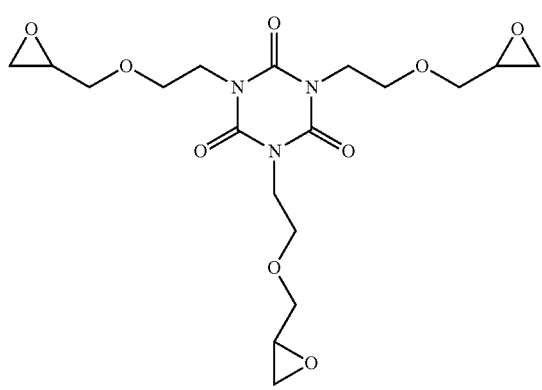
Formula (C-1-5)
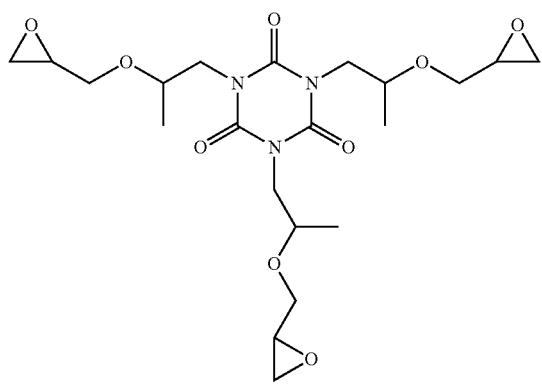
Formula (C-1-6)
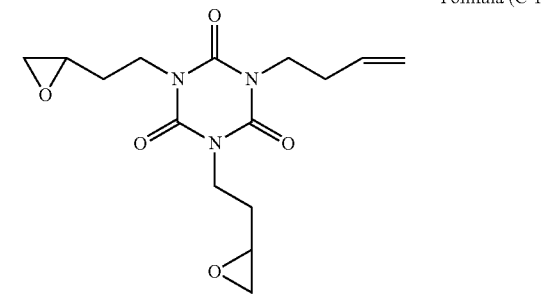
Formula (C-1-7)
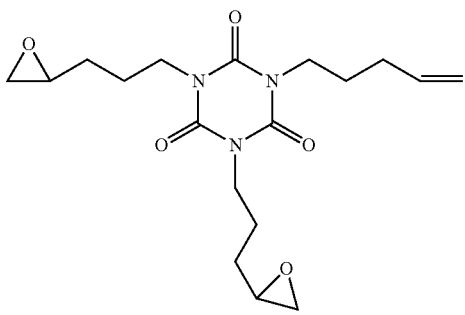
Formula (C-1-8)
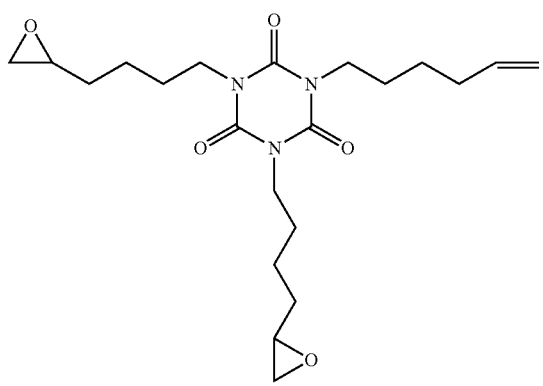
Formula (C-1-9)
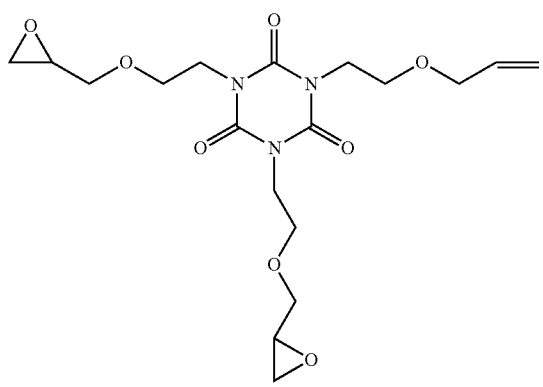
Formula (C-1-10)
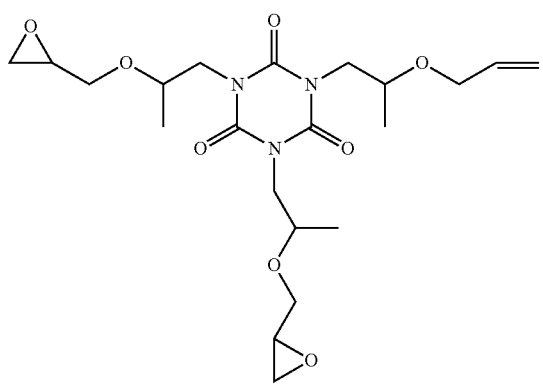

Formula (C-1-11)
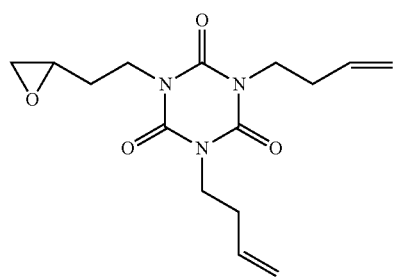
Formula (C-1-12)
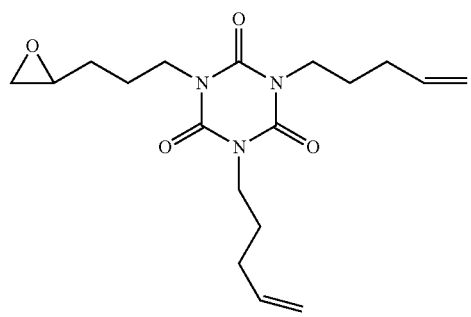
Formula (C-1-13)
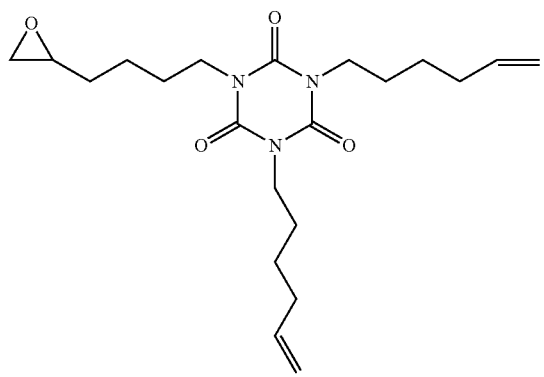
Formula (C-1-14)
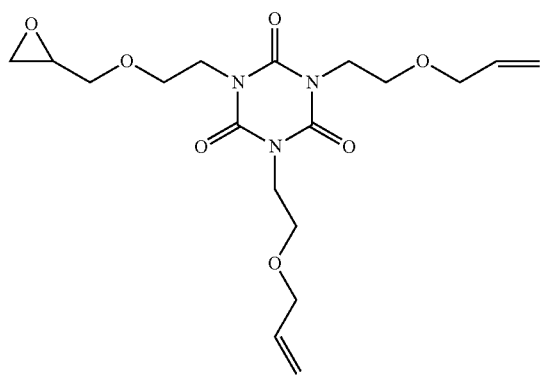
Formula (C-1-15)
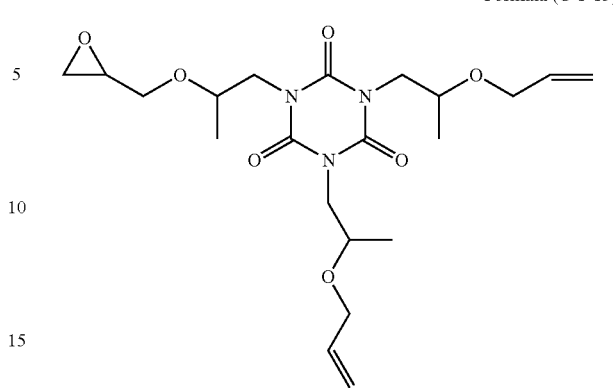
The crosslinkable compound of Formula (1) used in the present invention can be obtained, for example when the crosslinkable compound is a compound of Formula (C-1-2), by the method below.
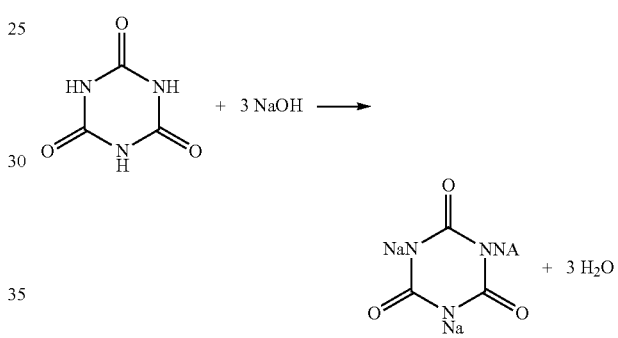
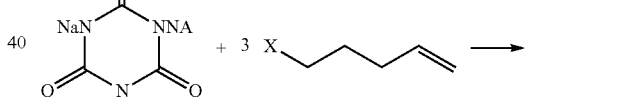
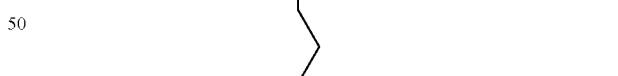
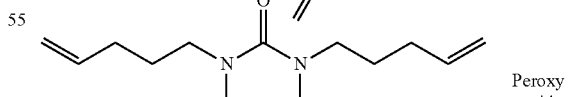
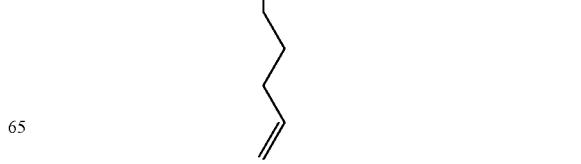

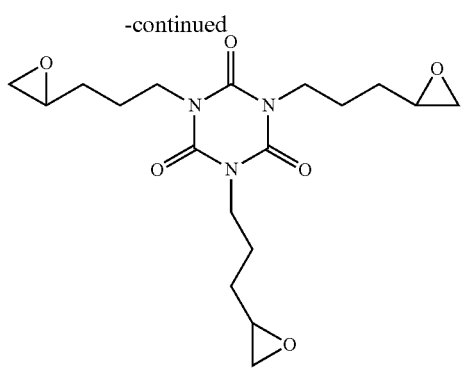

In the above reaction, first, isocyanuric acid is converted into isocyanuric acid Na salt with sodium hydroxide. This reaction can be effected in an aqueous solvent at 0 to 100° C. for 1 to 10 hour(s).

Next, isocyanuric acid Na salt is reacted with a halogenated alkene to obtain an alkene-substituted isocyanuric acid. This reaction can be effected, for example, in DMF (N,N-dimethylformamide) solvent at 0 to 150° C. for 1 to 10 hour(s). In the formula, X is a halogen atom and as the halogenated alkene, a monobromo alkene and a monochloro alkene can be used.

Then, the alkene-substituted isocyanuric acid is oxidized with a peroxy acid, so that an epoxy compound can be obtained. Here, as the peroxy acid, for example, m-chloroperbenzoic acid, peracetic acid, hydrogen peroxide-tungstic acid, and the like can be used. This reaction can be effected in a solvent such as methylene chloride and toluene at 0 to 110° C. for 1 to 10 hour(s).

The compounds of (C-1-1), (C-1-3), (C-1-6) to (C-1-8), and (C-1-11) to (C-1-13) can also be synthesized by the same method as described above.

The crosslinkable compound of Formula (1) used in the present invention can be obtained, for example when the crosslinkable compound is a compound of Formula (C-1-4), by the method below.

In the above reaction, a hydroxyalkyl isocyanurate is reacted with an epihalohydrin to obtain a tris(alkyleneoxyglycidyl) isocyanurate. As the hydroxyalkyl isocyanurate, hydroxyethyl isocyanurate or the like is used. In the formula, X is a halogen atom and examples of the epihalohydrin include epichlorohydrin and epibromohydrin. The reaction is effected in a solvent such as dioxane using as a catalyst, $BF_3$ or tin chloride at 0 to 100° C. for 1 to 10 hour(s). The compounds of Formulae (C-1-5), (C-1-9), (C-1-10), (C-1-14), and (C-1-15) above can also be synthesized by the same method as described above.

In the present invention, the compound in which $E^1$, $E^2$, and $E^3$ in Formula (1) have a structure of Formula (3) can be synthesized, for example, in the same manner as described above by the method below.

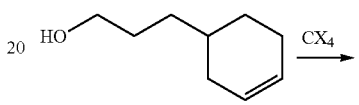

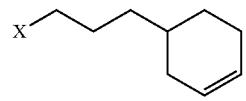

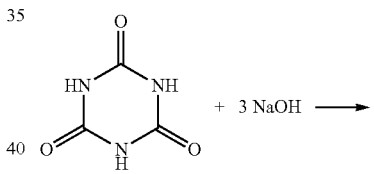

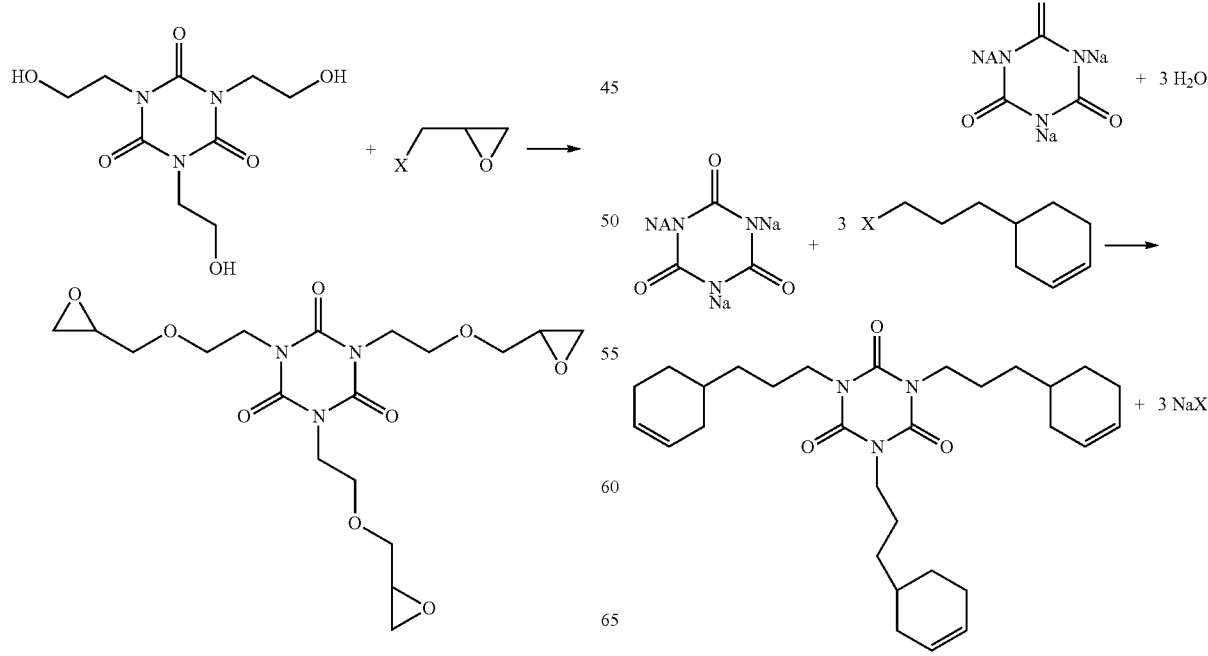

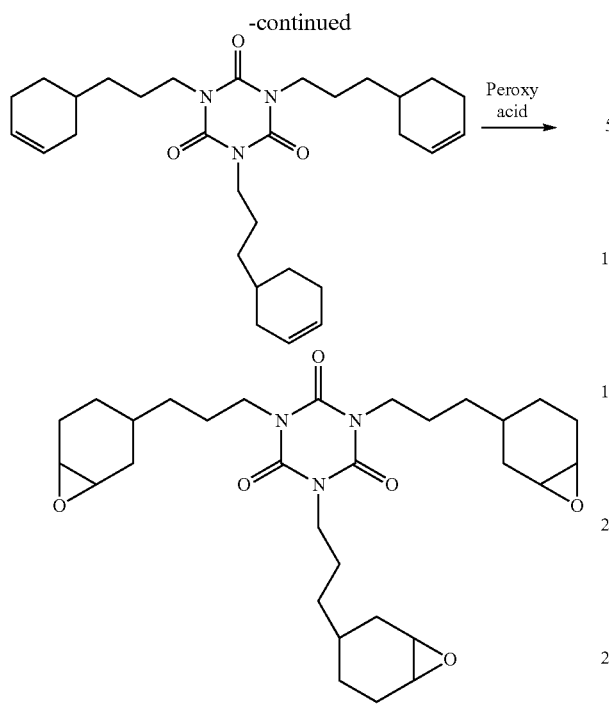 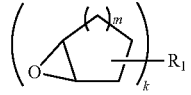

By the above reaction, an alcohol is converted into a halogenated alkene with a halogenated carbon. The reaction can be effected, for example, in dichloromethane solvent at 0 to 100° C. for 1 to 10 hour(s).

On the other hand, isocyanuric acid is converted into isocyanuric acid Na salt with sodium hydroxide. This reaction can be effected in an aqueous solvent at 0 to 100° C. for 1 to 10 hour(s).

Further, isocyanuric acid Na salt is reacted with a halogenated alkene to obtain an alkene-substituted isocyanuric acid. This reaction can be effected, for example, in DMF (N,N-dimethylformamide) solvent at 0 to 150° C. for 1 to 10 hour(s). In the formula, X is a halogen atom and as the halogenated alkene, a monobromo alkene and a monochloro alkene can be used.

Then, by oxidizing the alkene-substituted isocyanuric acid with a peroxy acid, an epoxy compound can be obtained. Here, as the peroxy acid, for example, m-chloroperbenzoic acid, peracetic acid, hydrogen peroxide-tungstic acid, and the like can be used. This reaction can be effected in a solvent such as methylene chloride and toluene at 0 to 110° C. for Ito 10 hour(s).

In the present invention, the crosslinkable compound (C-1) of Formula (1) [for example, compounds of Formulae (C-1-1) to (C-1-15)] is used in combination with a crosslinkable compound (C-2) having at least two epoxy groups and having a structure other than (C-1), that is, there can be prepared a positive resist composition containing (C-1) and (C-2) in a mass ratio (C-1)/[(C-1)+(C-2)] of 1% by mass, or 1.5% by mass or more, or 50 to 100% by mass. This mass ratio (C-1)/[(C-1)+(C-2)] may be 100% by mass, that is, the crosslinkable compound (C-1) may be individually used. However, from the viewpoint of the production cost, an epoxy compound prepared by mixing the crosslinkable compound (C-1) with the crosslinkable compound (C-2) may also be prepared.

Here, the compound (C-1) is a general term for a group of compounds (C-1) represented by the compounds (C-1-1) to (C-1-15) and exemplified compounds thereof. The compound (C-2) is a general term for a group of compounds (C-2) represented by the compounds (C-2-1) to (C-2-7) below and exemplified compounds thereof.

The compound (C-1) can be used either individually or in combination with an arbitral crosslinkable compound capable of being crosslinked with a hydroxy group or other organic groups in the component (C-1).

The crosslinkable compound (C-2) used in combination with the component (C-1) is shown below.

For example, a compound of Formula (C-2-1):

Formula (C-2-1)

$$\left( \underset{O}{\triangle} \right)_m R_1 \Big)_k$$

(where k is an integer of 2 to 10; m is an integer of 0 to 4; and $R_1$ is a k-valent organic group) having a cycloalkene oxide structure can be used.

Specific examples of the compound of Formula (C-2-1) include a compound of Formula (C-2-2):

Formula (C-2-2)

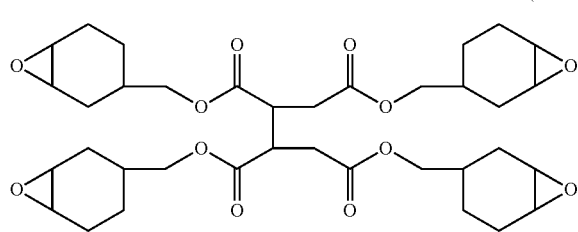

having a cyclohexene oxide structure.

Specific examples thereof also include the commercially available products exemplified below.

The commercially available products include: Epolead GT-401, GT-403, GT-301, GT-302, Celloxide 2021, and Celloxide 3000 (trade names; manufactured by Daicel Chemical Industries, Ltd.); and alicyclic epoxy resins such as Denacol EX-252 (trade name; manufactured by Nagase ChemteX Corporation), CY175, CY177, and CY179 (trade names; manufactured by CIBA-GEIGY A. G. (present: BASF)), Araldite CY-182, CY-192, and CY-184 (trade names; manufactured by CIBA-GEIGY A.G. (present: BASF)), Epiclon 200 and 400 (trade names; manufactured by DIC Corporation), and Epikote (present: jER) 871 and 872 (trade names; manufactured by Yuka Shell Epoxy Kabushiki Kaisha (present: Mitsubishi Chemical Corporation)).

Among them, from the viewpoints of process resistance such as heat resistance, solvent resistance, and long-period baking resistance and transparency, preferred are Epolead GT-401, GT-403, GT-301, and GT-302; and Celloxide 2021 and Celloxide 3000 which have a cyclohexene oxide structure.

As the crosslinkable compound, a compound having an oxysilane structure of Formula (C-2-3):

Formula (C-2-3)

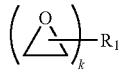

(where k is an integer of 2 to 10; and $R_1$ is a k-valent organic group) can be used.

Specific examples of the compound of Formula (C-2-3) include compounds of Formula (C-2-4):

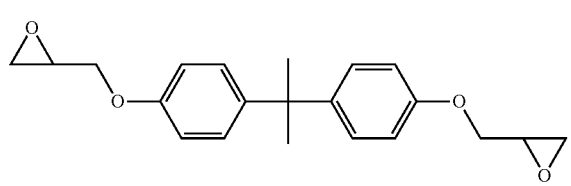

Formula (C-2-4)

Specific examples thereof also include the commercially available products exemplified below.

The commercially available products include: bisphenol A-type epoxy resins such as Epikote (present: jER) 828, 834, 1001, and 1004 (trade names; manufactured by Japan Epoxy Resins Co., Ltd. (present: Mitsubishi Chemical Corporation)), and Epiclon 850, 860, and 4055 (trade names; manufactured by DIC Corporation); bisphenol F-type epoxy resins such as Epikote (present: jER) 807 (trade name; manufactured by Japan Epoxy Resins Co., Ltd. (present: Mitsubishi Chemical Corporation)) and Epiclon 830 (trade name; manufactured by DIC Corporation); phenol novolac-type epoxy resins such as Epiclon N-740, N-770, and N-775 (trade names; manufactured by DIC Corporation) and Epikote (present: jER) 152 and 154 (trade names; manufactured by Japan Epoxy Resins Co., Ltd. (present: Mitsubishi Chemical Corporation)); cresol novolac-type epoxy resins such as Epiclon N-660, N-665, -670, N-673, N-680, N-695, N-665-EXP, and N-672-EXP (trade names; manufactured by DIC Corporation); glycidyl amine-type epoxy resins such as Epiclon 430 and 430-L (trade names; manufactured by DIC Corporation), TETRAD-C and TETRAD-X (trade names; manufactured by Mitsubishi Gas Chemical Company, Inc.), Epikote (present: jER) 604 and 630 (trade names; manufactured by Japan Epoxy Resins Co., Ltd. (present: Mitsubishi Chemical Corporation)), Sumiepoxy ELM 120, Sumiepoxy ELM 100, Sumiepoxy ELM 434, and Sumiepoxy ELM 434 HV (trade names; manufactured by Sumitomo Chemical Co., Ltd.), YH-434 and YH-434 L (trade names; manufactured by Tohto Kasei Co., Ltd. (present: Nippon Steel Chemical Co., Ltd.)), and Araldite MY-720 (trade name; manufactured by Asahi Ciba Co., Ltd.).

As the crosslinkable compound, a compound having a partial structure of Formula (C-2-5):

—$CH_2$—O—$R_1$    Formula (C-2-5)

(where $R_1$ is a $C_{1-6}$ alkyl group or a hydrogen atom) can be used.

Examples of the $C_{1-6}$ alkyl group include a methyl group, an ethyl group, a propyl group, an isopropyl group, a butyl group, a pentyl group, and a hexyl group.

The crosslinkable compound having a partial structure of Formula (C-2-5) is not particularly limited so long as the compound is a compound having a hydroxymethyl group or an alkoxymethyl group and preferred is a compound in which the hydroxymethyl group or the alkoxymethyl group is bonded to a nitrogen atom, that is, a compound containing an N-hydroxymethyl group or an N-alkoxymethyl group. Specific examples of such a compound include compounds of Formula (C-2-6) and Formula (C-2-7):

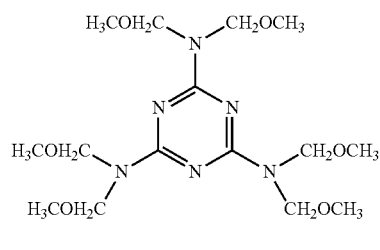

Formula (C-2-6)

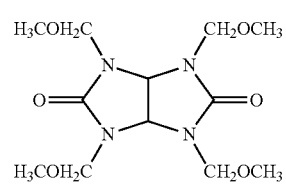

Formula (C-2-7)

and the following commercially available products.

Specific examples of the commercially available product include hexamethoxymethylmelamine, tetramethoxymethylbenzoguanamine, 1,3,4,6-tetrakis (methoxymethyl)glycoluril, 1,3,4,6-tetrakis (butoxymethyl)glycoluril, 1,3,4,6-tetrakis (hydroxymethyl)glycoluril, 1,3-bis(hydroxymethyl) urea, 1,1,3,3-tetrakis (butoxymethyl) urea, 1,1,3,3-tetrakis (methoxymethyl)urea, 1,3-bis (hydroxymethyl)-4,5-dihydroxy-2-imidazolinone, and 1,3-bis (methoxymethyl)-4,5-dimethoxy-2-imidazolinone. Specific examples of the commercially available product include, for example: methoxymethyl-type melamine compounds such as Cymel 300, Cymel 301, Cymel 303, and Cymel 350 (trade names; manufactured by Mitsui Cytec, Ltd. (present: Nihon Cytec Industries Inc.)); butoxymethyl-type melamine compounds such as Mycoat 506 and Mycoat 508 (trade names; manufactured by Mitsui Cytec, Ltd. (present: Nihon Cytec Industries Inc.)); glycoluril compounds such as Cymel 1170 and Powderlink 1174 (trade names; manufactured by Mitsui Cytec, Ltd. (present: Nihon Cytec Industries Inc.)); methylated urea resins such as UFR 65 (trade names; manufactured by Mitsui Cytec, Ltd. (present: Nihon Cytec Industries Inc.)); butylated urea resins such as UFR 300, U-VAN 10560, U-VAN 10R, and U-VAN 11HV (trade names; manufactured by Mitsui Cytec, Ltd. (present: Nihon Cytec Industries Inc.)); and urea/formaldehyde-based resins such as Beckamine J-3005, Beckamine P-955, and Beckamine N (trade names; manufactured by DIC Corporation).

Examples of the crosslinkable compound (C-2) include polymers produced using an acrylamide compound or a methacrylamide compound that are substituted with a hydroxymethyl group or an alkoxymethyl group such as N-hydroxymethylacrylamide, N-methoxymethylmethacrylamide, N-ethoxymethylacrylamide, and N-butoxymethylmethacrylamide. Examples of such a polymer include poly (N-butoxymethylacrylamide), a copolymer of N-butoxymethylacrylamide with styrene, a copolymer of N-hydroxymethylmethacrylamide with methyl methacrylate, a copolymer of N-ethoxymethylmethacrylamide with benzyl methacrylate, and a copolymer of N-butoxymethylacrylamide, benzyl methacrylate, and 2-hydroxypropyl methacrylate.

These crosslinkable compounds (C-2) may be used individually or in combination of two or more types thereof with a compound as the component (C-1).

[Component (E): Surfactant]

In the present invention, for the purpose of enhancing applicability, a surfactant (E) may be added to the composition. The surfactant is not particularly limited, and examples thereof include fluorinated surfactants, silicon-based surfactants, and nonionic surfactants.

As the component (E), these surfactants may be used individually or in combination of two or more types thereof.

Among these surfactants, in terms of high applicability enhancing effect, a fluorinated surfactant is preferred. Specific examples of the fluorinated surfactant include EFTOP EF 301, EF 303, and EF 352 (trade names; manufactured by Tohkem Products Corporation. (present: Mitsubishi Materials Electronic Chemicals Co., Ltd.)), MEGAFAC F 171, F 173, R-30, R-08, R-90, BL-20, and F-482 (trade names; manufactured by DIC Corporation), Fluorad FC 430 and FC 431 (trade names; manufactured by Sumitomo 3M Limited), and Asahi Guard AG 710, Surflon S-382, SC 101, SC 102, SC 103, SC 104, SC 105, and SC 106 (trade names; manufactured by Asahi Glass Co., Ltd.), to which the specific examples are not limited.

The additive amount of the component (E) in the positive resist composition of the present invention in the solid content is 0.0008 to 4.5% by mass, preferably 0.0008 to 2.7% by mass, more preferably 0.0008 to 1.8% by mass. When the additive amount of the surfactant is more than 4.5% by mass, unevenness is easily caused in the coating film. On the other hand, when the additive amount is less than 0.0008% by mass, striation or the like is easily caused in the coating film.

[Component (F): Adhesion Accelerator]

In the present invention, to the positive resist composition for the purpose of enhancing the adhesion to a substrate after development, an adhesion accelerator (F) may be added. Examples of the adhesion accelerator include: chlorosilanes such as trimethylchlorosilane, dimethylvinylchlorosilane, methyldiphenylchlorosilane, and chloromethyldimethylchlorosilane; alkoxysilanes such as trimethylmethoxysilane, dimethyldiethoxysilane, methyldimethoxysilane, dimethylvinylethoxysilane, diphenyldimethoxysilane, and phenyltriethoxysilane; silazanes such as hexamethyldisilazane, N,N'-bis(trimethylsilyl)urea, dimethyltrimethylsilylamine, and trimethylsilylimidazole; silanes such as vinyltrichlorosilane, γ-chloropropyltrimethoxysilane, γ-aminopropyltriethoxysilane, γ-methacryloxypropyltrimethoxysilane, γ-glycidoxypropyltrimethoxysilane, and γ-(N-piperidinyl)propyltrimethoxysilane; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; urea compounds such as 1,1-dimethylurea and 1,3-dimethylurea; and thiourea compounds.

As the component (F), these adhesion accelerators may be used individually or in combination of two or more types thereof. The additive amount of the adhesion accelerator in the solid content is usually 18% by mass or less, preferably 0.0008 to 9% by mass, more preferably 0.04 to 9% by mass. When the additive amount of the adhesion accelerator is more than 18% by mass, heat resistance of the coating film may be lowered. On the other hand, when the additive amount is less than 0.0008% by mass, satisfactory effect of the adhesion accelerator may not be obtained.

As other additives, if necessary, there may further be added to the composition a pigment, a dye, a preservation stabilizer, an antifoamer, a dissolution accelerator such as a polyphenol and a poly-carboxylic acid, and the like.

The positive resist composition of the present invention containing the above components is preferably a positive resist composition, when formed into a composition film having a thickness of 1.0 μm, having a coating film physical property of 80% or more that is a transmittance relative to light having a wavelength of 400 to 730 nm.

[Pattern Forming Method]

By applying the positive resist composition of the present invention onto a base material such as a glass substrate, a silicon wafer, an oxide film, a nitride film, and a substrate coated with a metal such as aluminum, molybdenum, and chromium by a rotation coating, a flow coating, a roll coating, a slit coating, a slit coating followed by a rotation coating, an inkjet coating, or the like, and by pre-drying (pre-baking) the composition using a hot plate, an oven, or the like, a coating film can be formed. At this time, pre-drying is performed preferably under conditions of at a temperature of 80° C. to 130° C. and for 30 to 600 seconds. However, if necessary, the condition can be accordingly selected. The thickness of the coating film may be selected from a range of 0.01 μm to around 10 mm according to the application of the cured film.

On the above obtained coating film, a mask having a predetermined pattern is fitted, and by irradiating the coating film with light such as an ultraviolet ray and developing the coating film with an alkaline developer, there can be obtained a relief pattern having a sharp edge face from which an exposed portion has been washed away.

The wavelength of light used for irradiation or exposure is, for example 150 to 800 nm, preferably 150 to 600 nm, further preferably 200 to 400 nm, particularly preferably around 300 to 400 nm. Although the amount of an irradiation light is varied depending on the thickness of the coating film, it may be, for example 2 to 20,000 mJ/cm$^2$, preferably 5 to around 5,000 mJ/cm$^2$.

In order to suppress the influence of a standing wave on the pattern shape, or in order to adjust the crosslinking degree of the crosslinkable compound (C) with the above-described polymer (A) or the 1,2-naphthoquinone diazide compound (B), a post exposure bake (PEB) can be performed.

The developer used during development is not particularly limited so long as the developer is an alkaline aqueous solution. Specific examples of the developer include: an aqueous solution of an alkali metal hydroxide such as potassium hydroxide, sodium hydroxide, potassium carbonate, and sodium carbonate; an aqueous solution of quaternary ammonium hydroxide such as tetramethylammonium hydroxide, tetraethylammonium hydroxide, and choline; and an aqueous solution of an amine such as ethanolamine, propylamine, and ethylenediamine.

The alkaline developer is an aqueous solution of generally 10% by mass or less, preferably 0.1 to 3.0% by mass. To the developer, alcohols or surfactants may be added to be used, and the additive amount of these additives is preferably 0.05 to 10 parts by mass, relative to 100 parts by mass of the developer.

Among them, a 0.1 to 2.38% by mass tetramethylammonium hydroxide aqueous solution is generally used as the developer for the photoresist, so that the positive resist of the present invention can be developed using this solution without causing a problem such as swelling.

As the developing method, any one of a puddle development method, a dipping method, and a vibration immersing method may be used. At this time, the developing time is usually 15 to 180 seconds.

After the development, by performing a flush washing for 20 to 90 seconds and by air-drying with compressed air or compressed nitrogen or with spinning to remove a water content on the substrate, a coating film on which a pattern is formed can be obtained.

Thereafter, the whole surface of the coating film on which a pattern is formed is irradiated with light such as a ultraviolet ray produced using a high pressure mercury lamp, and by completely decomposing the component (B) (1,2-naphthoquinonediazide compound) remaining in the pattern-shaped coating film, transparency of the coating film is enhanced.

Subsequently, by heating the coating film using a hot plate, an oven, or the like, the coating film is subjected to a curing treatment (hereinafter, called as "post bake"), and thus, a coating film excellent in heat resistance, transparency, planarizing property, low water absorbency, and chemical resistance and having an advantageous relief pattern can be obtained.

The post bake may be performed by heating using a heating apparatus such as a hot plate and an oven at a predetermined temperature such as 140° C. to 260° C. for a predetermined time such as 3 to 30 minutes on a hot plate and 30 to 90 minutes in an oven.

Thus, a cured film having an objective advantageous pattern shape can be obtained. The cured film is excellent in heat resistance, solvent resistance, and transparency and is suitably used in an interlayer insulation film, various insulation films, various protective films, a microlens, and the like.

EXAMPLES

Hereinafter, the present invention will be further described in more detail referring to Examples which should not be construed as limiting the scope of the present invention.

The abbreviations mean as follows. The structures of the compounds represented by the trade names below are as follows.

MAA: methacrylic acid,
MAIB: dimethyl 2,2'-azobisisobutyrate,
QD 1: a compound in which 2.0 mol (as a molar ratio) of D in Formula (B-5) is substituted with 1,2-naphthoquinone-2-diazide-5-sulfonyl chloride and 1.0 mol (as a molar ratio) of D is substituted with a hydrogen atom, relative to 1 mol of the compound of Formula (B-5), Compound of Formula (C-2-4) below: Epikote (present: jER) 828 (manufactured by Japan Epoxy Resins Co., Ltd. (present: Mitsubishi Chemical Corporation)), Formula (C-2-4)

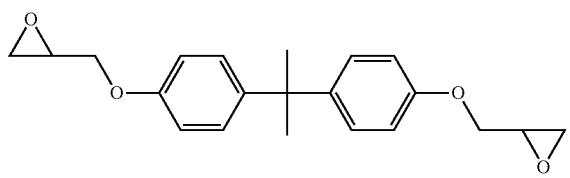

Compound of Formula (C-2-8) below: YH-434L (manufactured by Tohto Kasei Co., Ltd. (present: Nippon Steel Chemical Co., Ltd.)), Formula (C-2-8)

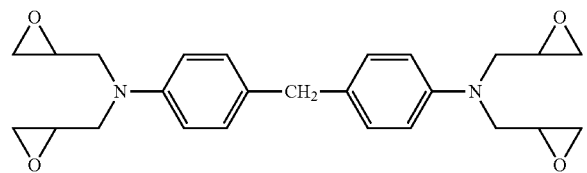

Compound of Formula (C-2-9) below: TETRAD-C (manufactured by Mitsubishi Gas Chemical Company, Inc.), Formula (C-2-9)

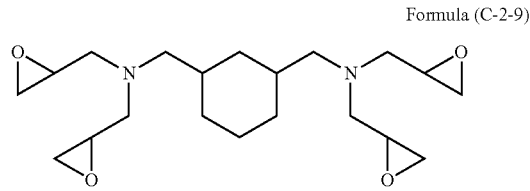 [SMILES: C1CC(CN(CC2CO2)CC2CO2)CC(CN(CC2CO2)CC2CO2)C1]

Compound of Formula (C-2-10) below: tris-(2,3-epoxypropyl)-isocyanurate (trade name; TEPIC) (manufactured by Nissan Chemical Industries, Ltd.), Formula (C-2-10)

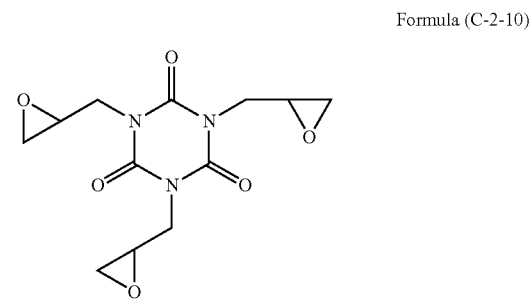 [SMILES: O=c1n(CC2CO2)c(=O)n(CC2CO2)c(=O)n1CC1CO1]

PGME: propylene glycol monomethyl ether,
PGMEA: propylene glycol monomethyl ether acetate,
MEGAFAC R30: fluorinated surfactant (trade name; manufactured by DIC Corporation),
TMAH: tetramethylammonium hydroxide, and
ARC-XHRiC-16: composition for forming an anti-reflective coating used in a resist underlayer (trade name; manufactured by Nissan Chemical Industries, Ltd.).

(Measurement of Number Average Molecular Weight and Weight Average Molecular Weight)

The number average molecular weight (hereinafter, called as Mn) and the weight average molecular weight (hereinafter, called as Mw) of a copolymer obtained according to the following Synthesis Examples were measured using a GPC apparatus (manufactured by JASCO Corporation; Shodex (registered trademark) column KF803L and KF804L) under the condition that the elution is performed by flowing an elution solvent THF in a column (temperature: 40° C.) at 1 mL/min. The following Mn and Mw are expressed in a value in terms of polystyrene.

(Synthesis Example 1: Synthesis of Crosslinkable Compound CL1)

In a reaction vessel, into a slurry in which 420 mL of water was added to 106 g of isocyanuric acid, 206 g of a 48% sodium hydroxide solution was dropped and the reaction was effected at a temperature of 60 to 70° C. for 2 hours. Then, water was distilled off from the resultant reaction mixture and the residue was washed with methanol and was dried to obtain 157.5 g of sodium isocyanurate as a white crystal. Into a reaction vessel equipped with a stirrer and a cooler, 400 mL of N,N-dimethylformamide as a solvent was charged and in the solvent, 157.5 g of sodium isocyanurate and 361.4 g of 5-bromo-1-pentene were reacted with each other at 120 to 125° C. for 6 hours. From the resultant reaction mixture, an inorganic salt was filtered off and the filtrate was extracted with toluene. The extract was washed with water and was dried and from the extract, the solvent was distilled off to obtain 205 g of tris 5-pentenyl isocyanurate as a light brown oily substance. Into a reaction vessel equipped with a stirrer and a cooler, 8,700 mL of methylene chloride as a solvent was charged and thereto, 205 g of tris 5-pentenyl isocyanurate was added. To the resultant reaction mixture, 815 g of m-chloroperbenzoic acid was slowly added at 30° C. or less and the reaction was effected at 25° C. for 4 hours. After the completion of the reaction, 3,000 mL of a 10% sodium hydrogen sulfite aqueous solution was slowly added to the reaction mixture at 20° C. or less and an insoluble matter was filtered off. To the filtrate, chloroform was added and the filtrate was solvent-extracted. The extract was fully washed with a 10% sodium hydrogen sulfite aqueous solution and a saturated sodium hydrogen carbonate solution and was dried and from the extract, the solvent was distilled off to obtain a crude product. The crude product was purified by silica gel chromatography to obtain 161.7 g of a transparent oily substance. The obtained epoxy compound was tris(4,5-epoxypentyl) isocyanurate corresponding to a compound of Formula (C-1-2).

The obtained crosslinkable compound of Formula (C-1-2) is hereinafter abbreviated as CL 1.

(Synthesis Example 2: Synthesis of Crosslinkable Compound CL2)

In a reaction vessel, into a slurry in which 420 mL of water was added to 106 g of isocyanuric acid, 206 g of a 48% sodium hydroxide solution was dropped and the reaction was effected at a temperature of 60 to 70° C. for 2 hours. Then, water was distilled off from the resultant reaction mixture and the residue was washed with methanol and was dried to obtain 157.5 g of sodium isocyanurate as a white crystal. Into a reaction vessel equipped with a stirrer and a cooler, 400 mL of N,N-dimethylformamide as a solvent was charged and in the solvent, 157.5 g of sodium isocyanurate and 327.4 g of 4-bromo-1-butene were reacted with each other at 120 to 125° C. for 6 hours. From the resultant reaction mixture, an inorganic salt was filtered off and the filtrate was extracted with toluene. The extract was washed with water and was dried and from the extract, the solvent was distilled off to obtain 179 g of tris 4-butenyl isocyanurate as a light brown oily substance. Into a reaction vessel equipped with a stirrer and a cooler, 8,700 mL of methylene chloride as a solvent was charged and thereto, 179 g of tris 4-butenyl isocyanurate was added. To the resultant reaction mixture, 815 g of m-chloroperbenzoic acid was slowly added at 30° C. or less and the reaction was effected at 25° C. for 4 hours. After the completion of the reaction, 3,000 mL of a 10% sodium hydrogen sulfite aqueous solution was slowly added to the reaction mixture at 20° C. or less and an insoluble matter was filtered off. To the filtrate, chloroform was added and the filtrate was solvent-extracted. The extract was fully washed with a 10% sodium hydrogen sulfite aqueous solution and a saturated sodium hydrogen carbonate solution and was dried and from the extract, the solvent was distilled off to obtain a crude product. The crude product was purified by silica gel chromatography to obtain 141.3 g of a transparent oily substance. The obtained epoxy compound was tris(3,4-epoxybutyl) isocyanurate corresponding to a compound of Formula (C-1-1).

The obtained crosslinkable compound of Formula (C-1-1) is hereinafter abbreviated as CL 2.

(Synthesis Example 3: Synthesis of Crosslinkable Compound CL3)

In a reaction vessel, into a slurry in which 420 mL of water was added to 106 g of isocyanuric acid, 206 g of a 48% sodium hydroxide solution was dropped and the reaction was effected at a temperature of 60 to 70° C. for 2 hours. Then, water was distilled off from the resultant reaction mixture and the residue was washed with methanol and was dried to obtain 157.5 g of sodium isocyanurate as a white crystal. Into a reaction vessel equipped with a stirrer and a cooler, 400 mL of N,N-dimethylformamide as a solvent was charged and in the solvent, 157.5 g of sodium isocyanurate and 395.4 g of 6-bromo-1-hexene were reacted with each other at 120 to 125° C. for 6 hours. From the resultant reaction mixture, an inorganic salt was filtered off and the filtrate was extracted with toluene. The extract was washed with water and was dried and from the extract, the solvent was distilled off to obtain 230.8 g of tris 6-hexenyl isocyanurate as a light brown oily substance. Into a reaction vessel equipped with a stirrer and a cooler, 8,700 mL of methylene chloride as a solvent was charged and thereto, 230.8 g of tris 6-hexenyl isocyanurate was added. To the resultant reaction mixture, 815 g of m-chloroperbenzoic acid was slowly added at 30° C. or less and the reaction was effected at 25° C. for 4 hours. After the completion of the reaction, 3,000 mL of a 10% sodium hydrogen sulfite aqueous solution was slowly added to the reaction mixture at 20° C. or less and an insoluble matter was filtered off. To the filtrate, chloroform was added and the filtrate was solvent-extracted. The extract was fully washed with a 10% sodium hydrogen sulfite aqueous solution and a saturated sodium hydrogen carbonate solution and was dried and from the extract, the solvent was distilled off to obtain a crude product. The crude product was purified by silica gel chromatography to obtain 182.1 g of a transparent oily substance. The obtained epoxy compound was tris(5,6-epoxyhexyl) isocyanurate corresponding to a compound of Formula (C-1-3).

The obtained crosslinkable compound of Formula (C-1-3) is hereinafter abbreviated as CL 3.

(Synthesis Example 4: Synthesis of Alkali-Soluble Polymer (P-1) as Component (A))

Styrene (60.0 g) and MAA (21.2 g) used as monomer components constituting the component (A) and MAIB (4.1 g) used as a radical-polymerization initiator were subjected to a polymerization reaction in 1,4-dioxane (340.0 g) for 10 hours while stirring the reaction mixture and heating-refluxing the reaction mixture at the heating-refluxing temperature. The reaction solution was cooled down to room temperature and was charged into a large amount of n-hexane to reprecipitate a polymer, and the resultant precipitate was dried by heating at 50° C. to obtain a white powder of the component (A): the polymer (P-1) having Mn of 6,000 and Mw of 14,000.

Example 1

The component (A): 2.0 g of the polymer (P-1), the component (B): 0.6 g of QD 1, the component (C): 0.6 g of CL 1, the component (D): a solvent mixture of 8.88 g of PGME and 8.88 g of PGMEA, and the component (E): 0.01 g of MEGA-FAC R30 were mixed and the resultant mixture was stirred at room temperature for 1 hour to prepare a homogeneous solution to obtain a positive resist composition.

Example 2

The component (A): 2.0 g of the polymer (P-1), the component (B): 0.6 g of QD 1, the component (C): 0.6 g of CL 2, the component (D): a solvent mixture of 8.88 g of PGME and 8.88 g of PGMEA, and the component (E): 0.01 g of MEGA-FAC R30 were mixed and the resultant mixture was stirred at room temperature for 1 hour to prepare a homogeneous solution to obtain a positive resist composition.

Example 3

The component (A): 2.0 g of the polymer (P-1), the component (B): 0.6 g of QD 1, the component (C): 0.6 g of CL 3, the component (D): a solvent mixture of 8.88 g of PGME and 8.88 g of PGMEA, and the component (E): 0.01 g of MEGAFAC R30 were mixed and the resultant mixture was stirred at room temperature for 1 hour to prepare a homogeneous solution to obtain a positive resist composition.

Comparative Example 1

The component (A): 2.0 g of the polymer (P-1), the component (8): 0.6 g of QD 1, the component (C): 0.6 g of a compound of Formula (C-2-4), the component (D): a solvent mixture of 8.88 g of PGME and 8.88 g of PGMEA, and the component (E): 0.01 g of MEGAFAC R30 were mixed and the resultant mixture was stirred at room temperature for 1 hour to prepare a homogeneous solution to obtain a positive resist composition.

Comparative Example 2

The component (A): 2.0 g of the polymer (P-1), the component (B): 0.6 g of QD 1, the component (C): 0.6 g of a compound of Formula (C-2-8), the component (D): a solvent mixture of 8.88 g of PGME and 8.88 g of PGMEA, and the component (E): 0.01 g of MEGAFAC R30 were mixed and the resultant mixture was stirred at room temperature for 1 hour to prepare a homogeneous solution to obtain a positive resist composition.

Comparative Example 3

The component (A): 2.0 g of the polymer (P-1), the component (B): 0.6 g of QD 1, the component (C): 0.6 g of a compound of Formula (C-2-9), the component (D): a solvent mixture of 8.88 g of PGME and 8.88 g of PGMEA, and the component (E): 0.01 g of MEGAFAC R30 were mixed and the resultant mixture was stirred at room temperature for 1 hour to prepare a homogeneous solution to obtain a positive resist composition.

Comparative Example 4

The component (A): 2.0 g of the polymer (P-1), the component (B): 0.6 g of QD 1, the component (C): 0.6 g of a compound of Formula (C-2-10), the component (D): a solvent mixture of 8.88 g of PGME and 8.88 g of PGMEA, and the component (E): 0.01 g of MEGAFAC R30 were mixed. The resultant mixture was stirred at room temperature for 12 hours; however, a homogeneous solution could not be obtained.

Each of the positive resist compositions obtained in Examples 1 to 3 and Comparative Examples 1 to 3 was subjected to measurements of the resolution, the light transmittance after baking, and the refractive index to be evaluated.

(Evaluation of Resolution)

All processes other than the following exposure process were performed using an automatic applying and developing apparatus (ACT-8; manufactured by Tokyo Electron Ltd.). ARC-XHRiC-16 was applied on a silicon wafer using a spin coater and the resultant coating film was baked at 175° C. for 60 seconds to form an anti-reflective coating. On the anti-reflective coating, each of the positive resist compositions obtained in Examples 1 to 3 and Comparative Examples 1 to 3 was applied using a spin coater, and the resultant coating film was pre-baked at 80° C. for 90 seconds to form a coating film having a film thickness of 0.6 µm. The resultant coating film was irradiated with an ultraviolet ray having a wavelength of 365 nm through a test mask using an i-line stepper (NSR2205 i 12D; manufactured by Nikon Corporation). Then, the coating film was subjected to post exposure bake at 80° C. for 90 seconds, to development by a 0.2% TMAH aqueous solution having a temperature of 23° C. for 50 seconds, and to ultrapure water washing to form a positive pattern.

The resultant pattern was observed under a scanning electron microscope (S4800; manufactured by Hitachi, Ltd.). A pattern in which a dot pattern of 2 µm was formed in a rectangle shape without peeling was evaluated as "advantageous resolution" with "O", and a pattern in which the pattern shape was not a rectangle shape or was not resolved was evaluated with "X". The obtained result is shown in Table 1.

(Evaluation of Transparency)

On a quartz substrate, each of the positive resist compositions obtained in Examples 1 to 3 and Comparative Examples 1 to 3 was applied using a spin coater and the positive resist composition was pre-baked by heating the positive resist composition on a hot plate at 80° C. for 3 minutes to form a coating film having a film thickness of 1.0 µm. Then, the whole surface of the resultant coating film was irradiated with an ultraviolet light having an irradiance at a wavelength of 365 nm of 1,000 mJ/cm$^2$ using an ultraviolet ray irradiating apparatus (PLA-501 (F); manufactured by Canon Inc.) and the coating film was post-baked by heating the coating film at 160° C. for 5 minutes and at 200° C. for 5 minutes and subsequently, was high temperature-baked by heating the coating film at 250° C. for 10 minutes.

With respect to the coating film after the ultraviolet light irradiation and the coating film after the post-bake, the light transmittance relative to light having a wavelength of 400 nm was measured using an ultraviolet ray-visible spectrophotometer (UV-2550; manufactured by Shimadzu Corporation). The obtained result is shown in Table 1.

(Evaluation of Chemical Resistance)

On a silicon substrate, each of the positive resist compositions obtained in Examples 1 to 3 and Comparative Examples 1 to 3 was applied using a spin coater and the positive resist composition was pre-baked by heating the positive resist composition on a hot plate at 80° C. for 4 minutes to form a coating film having a film thickness of 1.0 µm. Then, the whole surface of the resultant coating film was irradiated with an ultraviolet light having an irradiance at a wavelength of 365 nm of 500 mJ/cm$^2$ using an ultraviolet ray irradiating apparatus (PLA-501 (F); manufactured by Canon Inc.) and the coating film was post-baked at 160° C. for 5 minutes and at 200° C. for 5 minutes.

The prepared coating film was immersed in PGME or PGMEA for 1 minute and a case where a residual film remained was evaluated as advantageous solvent resistance with "O" and a case where a residual film disappeared was evaluated with "X". The obtained result is shown in Table 1.

TABLE 1

| | | Light transmittance (%) | | Solvent resistance | |
|---|---|---|---|---|---|
| | Resolution | after post-bake | after high temperature-bake | PGME | PGMEA |
| Example 1 | O | 98 | 95 | O | O |
| Example 2 | O | 95 | 94 | O | O |
| Example 3 | O | 96 | 95 | O | O |
| Comparative Example 1 | X | 97 | 91 | X | X |
| Comparative | X | 95 | 75 | O | O |

TABLE 1-continued

| | Reso-lution | Light transmittance (%) | | Solvent resistance | |
| | | after post-bake | after high temperature-bake | PGME | PGMEA |
|---|---|---|---|---|---|
| Example 2 | | | | | |
| Comparative Example 3 | X | 93 | 86 | ○ | ○ |
| Comparative Example 4 | — | — | — | — | — |

* In Comparative Example 4, a homogeneous solution (positive resist composition) could not be obtained.

As the crosslinkable compound, CL 1 to CL 3 which are the compounds of Formula (1) exhibited high solubility in a solvent and the positive resist compositions of Examples 1 to 3 using these crosslinkable compounds could form a homogeneous coating film when resist films were formed from these positive resist compositions.

Then, as shown in Table 1, any one of the coating films obtained from the positive resist compositions of Examples 1 to 3 had advantageous resolution and exhibited a high light transmittance even after the post-bake was performed.

In Examples 1 to 3, in the case of Example 1 where as the component (C), there was used a compound in which the alkylene group as $R^1$, $R^2$, or $R^3$ in the crosslinkable compound of General Formula (1) was an ethylene group (that is, as the crosslinkable compound, tris(4,5-epoxypentyl) isocyanurate was used) and in the case of Example 3 where as the component (C), there was used a compound in which the alkylene group as $R^1$, $R^2$, or $R^3$ in the crosslinkable compound of General Formula (1) was a propylene group (that is, as the crosslinkable compound, tris(5,6-epoxyhexyl) isocyanurate was used), it was resulted in that the light transmittance was enhanced higher than in the case of Example 2 where as the component (C), there was used a compound in which the alkylene group as $R^1$, $R^2$, or $R^3$ in the crosslinkable compound of General Formula (1) was a methylene group (that is, as the crosslinkable compound, tris(3,4-epoxybutyl) isocyanurate was used).

On the other hand, although the use of the compositions of Comparative Examples 1 and 3 exhibited a relatively high light transmittance even after the post bake was performed, it was resulted in that the coating films could not form an advantageous pattern after development and was poor in resolution.

With respect to the composition of Comparative Example 2, the light transmittance was extremely lowered after the post bake was performed and the coating film could not form an advantageous pattern after development.

In Comparative Example 4, as described above, a homogeneous solution could not be obtained. This is because, the crosslinkable compound used in Comparative Example 4 could not completely be dissolved in the solvent at room temperature, so that although the film formation was attempted, a homogeneous coating film could not be formed, so that the positive resist composition of Comparative Example 4 could not be evaluated as the positive resist composition.

INDUSTRIAL APPLICABILITY

The positive resist composition according to the present invention is excellent in terms of high sensitivity, heat resistance, and transparency, is suitable for a material for forming a microlens used in a solid-state image sensor and the like, can miniaturize the solid-state image sensor, and is a material that has weatherability required when the microlens is mounted on a vehicle.

RELATED-ART DOCUMENT

Patent Document

Patent Document 1: US Patent Application Publication No. 2007/0295956
Patent Document 2: US Patent Application Publication No. 2007/0295983
Patent Document 3: US Patent Application Publication No. 2007/0299162

The invention claimed is:
1. A positive resist composition comprising:
a component (A): an alkali-soluble polymer;
a component (B): a compound having an organic group to be photolyzed to generate an alkali-soluble group;
a component (C): a crosslinkable compound of Formula (1):

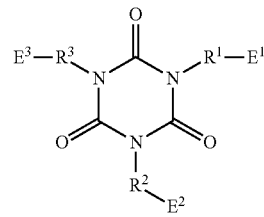

Formula (1)

where:
$R^1$, $R^2$, and, $R^3$ are independently a $C_{1-6}$ alkylene group or oxyalkylene group which are optionally branched; and
$E^1$, $E^2$, and $E^3$ are independently a group containing a structure of Formula (2) Formula (3), or Formula (7):

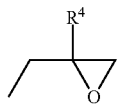

Formula (2)

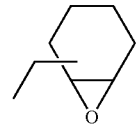

Formula (3)

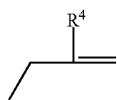

Formula (7)

where $R^4$ is a hydrogen atom or a methyl group; and
a component (D): a solvent.
2. The positive resist composition according to claim 1, wherein the alkali-soluble polymer as the component (A) is a polymer comprising a repeating unit that contains a hydroxy group, a carboxy group, or a combination thereof.

3. The positive resist composition according to claim 1, wherein the alkali-soluble polymer as the component (A) is a copolymer of a monomer having a hydroxy group, a carboxy group, or a combination thereof with a monomer having a hydrophobic group.

4. The positive resist composition according to claim 1, wherein the component (B) is a compound having a structure of Formula (4):

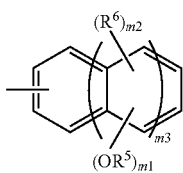

Formula (4)

where:

R$^5$ is a hydrogen atom or a structure of Formula (5):

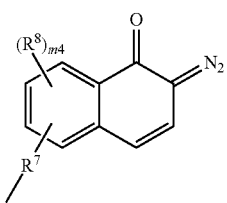

Formula (5)

where:

R$^7$ is a single bond or a —SO$_3$— group;

R$^8$ is a C$_{1-10}$alkyl group; and m4 is an integer of 0 to 3;

R$^6$ is a C$_{1-10}$ substituted or unsubstituted alkyl group, a halogen atom, or a C$_{1-10}$ alkoxy group; and m3 is an integer of 0 or 1, where when m3 is 0, m1 is an integer of 1 to 5 and m2 is an integer satisfying 0≤m2≤(5-m1), and when m3 is 1, m1 is an integer of 1 to 7 and m2 is an integer satisfying 0≤m2≤(7-m1);

with the proviso that R$^5$ is a structure of Formula (5) in an amount of 10 to 100% by mol, based on a total number of moles of the substituent R$^5$ contained in the compound having a structure of Formula (4).

5. The positive resist composition according to claim 4, wherein the component (B) is a compound of Formula (6):

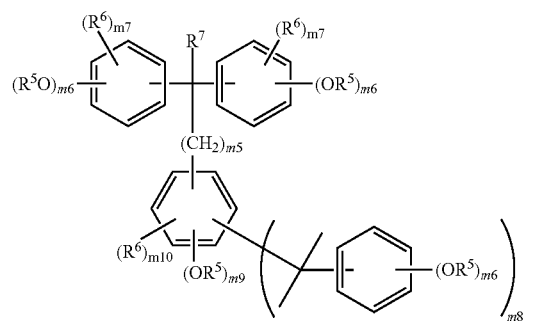

Formula (6)

where:

R$^5$ and R$^6$ are individually the same group as those defined in the above Formula (4);

R$^7$ is a hydrogen atom or a C$_{1-10}$ alkyl group;

m5 is an integer of 0 to 10;

m6 is an integer of 1 to 5;

m7 is an integer satisfying 0≤m7≤(5-m6);

m8 is an integer of 0 to 1;

m9 is an integer of 0 to 5; and m10 is an integer satisfying 0≤m10≤(5-m8-m9);

with the proviso that R$^5$ is a structure of Formula (5) in an amount of 10 to 100% by mol, based on the total number of moles of the substituent R$^5$ contained in the compound of Formula (6).

6. The positive resist composition according to claim 1, wherein in the crosslinkable compound as the component (C), E$^1$, E$^2$, and E$^3$ are independently a group containing a structure of Formula (2) or Formula (3).

7. The positive resist composition according to claim 1, wherein the positive resist composition, when formed into a composition film having a thickness of 1.0 μM, has a coating film physical property of 80% or more that is a transmittance relative to light having a wavelength of 400 to 730 nm.

8. A pattern forming method comprising:

applying the positive resist composition as claimed in claim 1 on a substrate; and subjecting the resultant coating to drying, exposure, and development.

9. The pattern forming method according to claim 8, comprising a heating process after exposure and before development.

10. A solid-state image sensor comprising a microlens or a planarizing film produced by the pattern forming method as claimed in claim 8.

* * * * *